United States Patent [19]
Kim et al.

[11] Patent Number: 5,861,163
[45] Date of Patent: Jan. 19, 1999

[54] **PROCESS FOR PREPARING A VACCINE AGAINST *PSEUDOMONAS AERUGINOSA* USING ATTENUATED STRAINS**

[75] Inventors: Hyun Su Kim, Seoul; Wan Je Park, Suwon; Wang Don Yoo, Seongnam; Kap Soo Noh, Seoul; Dong Eok Lee, Seoul; Suk Hoon Ha, Seoul; Ree An Yoo, Kwachun; Nam Joong Lee, Seoul; Yang Je Cho, Seoul; Sun Pyo Hong, Seoul; Je Hak Kim; Dal Hyun Kim, both of Suwon; Young Gi Kim, Seoul, all of Rep. of Korea

[73] Assignee: Cheil Jedang Corporation, Rep. of Korea

[21] Appl. No.: 773,330

[22] Filed: Dec. 24, 1996

Related U.S. Application Data

[60] Continuation-in-part of Ser. No. 370,157, Jan. 9, 1995, abandoned, which is a division of Ser. No. 141,601, Oct. 27, 1993, abandoned.

[30] Foreign Application Priority Data

Jun. 7, 1993 [KR] Rep. of Korea ...................... 93-10273
Jun. 7, 1993 [KR] Rep. of Korea ...................... 93-10281

[51] Int. Cl.$^6$ .......................... A61K 39/108; A61K 39/02
[52] U.S. Cl. ...................................... 424/260.1; 424/234.1
[58] Field of Search .............................. 424/260.1, 234.1

[56] References Cited

U.S. PATENT DOCUMENTS

| | | | |
|---|---|---|---|
| 3,674,863 | 7/1972 | Fisher ......................................... | 424/92 |
| 4,477,432 | 10/1984 | Hardie et al. ............................. | 424/85 |
| 4,482,483 | 11/1984 | Curry et al. ........................... | 260/112 R |
| 4,877,608 | 10/1989 | Lee et al. ................................ | 424/85.8 |

OTHER PUBLICATIONS

Stanislavsky et al Zh. Mikrobiol. Epidemiol Immunobiol 55:65–70 (Abstract Only), 1978.
Stanislavsky et al ACTA Microbiol Hunt 33:245–255 (Abstract Only, 1986.
Hasin et al. Biochim Biophy Acta 375:381–394 (Abstract Only), 1975.
Sawada et al., *The Journal of Infectious Diseases*, 150: 570–576, 1984.
Hancock et al., *Infection & Immunity*, 37: 166–171, 1982.
Collins et al., *Journal of Trauma*, 37: 166–171, 1982.
Schiller et al., *Arch. Immunol Ther. Exp.*, 29: 627–633, 1981 (Abstract only).
Hancock et al., *Molocular Microbiology*, 4(7), pp. 1069–1075, 1990.
Abe et al., *J. Exp. Med.*, 45: 355–359, 1975.
Sawada et al., *The Journal of Infectious Diseases*, 152: 1290–1299, 1985.
Collins et al., *FEMS Microbiology Immunology*, 64: 263–268, 1990.
Stanislavsky et al., *Vaccine*, 7: 562–566, 1989.
Hudson et al., *Practical Immunology*, 292–294, 1989.
Meadow et al., *Journal of General Microbiology*, 130: 631–655, 1984.
Luzar et al., *Infect & Immunity*, 50: 572–576, 1985.
McGroarty et al., *Infect & Immunity*, 58: 1030–1037, 1990.
Kropinski et al., *J. of Bact.*, 169: 1960–1966, 1987.
Cryz et al., *Infect & Immunity*, 44: 508–513, 1984.
Cripps et al., *Infection & Immunity*, 62: 1427–1436, 1994.
Engels et al., *Infect & Immunity*, 40: 182–189, 1985.
Miler et al., *J. Med. Microbiol.*, 10: 19–27, 1977.
Fujimaki et al., *Antimicrob. Agents Chemother*, 827–833, 1988.

*Primary Examiner*—Susan A. Loring
*Attorney, Agent, or Firm*—Pillsbury Madison & Sutro LLP

[57] ABSTRACT

The present invention relates to a vaccine prepared from an attenuated *Pseudomonas aeruginosa* strains which are obtained by isolating *Pseudomonas aeruginosa* in a pure state according to the Fisher-Devlin immunotype and then repeatedly purifying the isolated strain, particularly CFCPA 10142 (KCCM 10029), CFCPA 20215 (KCCM 10030), CFCPA 30720 (KCCM 10031), CFCPA 40057 (KCCM 10032), CFCPA 50243 (KCCM 10033), CFCPA 60534 (KCCM 10034) and CFCPA 70018 (KCCM 10035) strains. In addition, the present invention relates to a process for preparing the vaccine for immunization against *Pseudomonas aeruginosa* infection which contains cell wall proteins having molecular weights ranging from 10,000 to 100,000. The cell wall protein component of the attenuated strain is non-pathogenic and safe, and exhibits excellent antibody formation capacity and is useful for preparation of a vaccine and therapeutic agent. The cell wall proteins exhibit an excellent cross-protective efficacy for various *Pseudomonas aeruginosa* strains and a superior antibody inducing property.

7 Claims, 3 Drawing Sheets

FIG. 1

LANE 1. PRESTAINED LOW MOLECULAR WEIGHT MARKER (BIO-RAD)
LANE 2. PURIFIED CELL WALL PROTEINS OF P. AERUGINOSA
    CFCPA 30720 (LOT# 93041)
LANE 3. PURIFIED CELL WALL PROTEINS OF P. AERUGINOSA
    CFCPA 30720 (LOT# 93052)
LANE 4. PURIFIED CELL WALL PROTEINS OF P. AERUGINOSA
    CFCPA 30720 (LOT# 93061)
LANE 5. LOW MOLECULAR WEIGHT MARKER (PHARMACIA)

PROCESS FOR PREPARING A VACCINE AGAINST *PSEUDOMONAS AERUGINOSA* USING ATTENUATED STRAINS

CROSS-REFERENCE TO RELATED APPLICATIONS

This is a continuation-in-part application of U.S. patent application Ser. No. 08/370,157 filed Jan. 9, 1995, now abandoned, which is a division of U.S. patent application Ser. No. 08/141,601 filed Oct. 27, 1993, previously abandoned.

TECHNICAL FIELD

The present invention relates to a vaccine against *Pseudomonas aeruginosa* infections, and a process for preparing the vaccine. More specifically, the present invention relates to a novel vaccine prepared from an attenuated *Pseudomonas aeruginosa* strains which are obtained by isolating *Pseudomonas aeruginosa* in a pure state according to Fisher-Devlin immunotype and then repeatedly purifying the isolated strain by serial passages through mice, and a process for preparing the vaccine.

BACKGROUND ART

*Pseudomonas aeruginosa* is a motile gram-negative rod, approximately 0.5 $\mu$m×1.5–3.0 $\mu$m, with a single flagellum and occurs widely in soil, water, sewage and human intestine (See, Mol. Microbiol. 4, 1069–1075, 1990). *Pseudomonas aeruginosa* is a pathogenic strain causative of inveterate infections such as septicemia, generalized infection, chronic respiratory tract infection, cystic fibrosis, etc. The septicemia caused by *Pseudomonas aeruginosa* is a disease resulting from either the invasion of the microorganism itself or the secretion of its toxic components into the blood of patients who have lowered resistance due to surgery, laceration, trauma and the like. The presence of the toxin causes shock with high fever, reduced blood pressure, and other symptoms, which ultimately may lead to death. Furthermore, since *Pseudomonas aeruginosa* has been detected in urinary tract infections, interest in *Pseudomonas aeruginosa* has greatly increased. Accordingly, development of a medicinal agent(s) capable of effectively preventing or treating inveterate suppurative diseases, such as septicemia and urinary tract infections, caused by *Pseudomonas aeruginosa* is urgently needed. However, *Pseudomonas aeruginosa* strains are resistant to most antibiotic substances and an effective preventive or therapeutic agent for *Pseudomonas aeruginosa* infections has not been developed up to date. Thus, the lethality by *Pseudomonas aeruginosa* infections has increased over time.

*Pseudomonas aeruginosa* strains can be classified in various ways. One such classification system classifies the strains into seven (7) types according to Fisher immunotype [See, *J. Bacteriol.,* Vol. 98, No. 2, p. 835–836, May, 1969.] Another system is based on the 0-antigen group as proposed by Terada. Still another system is the International Antigenic Typing Scheme (IATS) classification system. In view of classification systems, the *Pseudomonas aeruginosa* strains most frequently occurring in *Pseudomonas aeruginosa*-infected patients are: 5/2a, 2c, 3, 7/3a, 3c, 1/4a, 4b, 6/5a, 5b, 4/6, 2/7a, 7b, 7c, /10a, /13, /12, /11 and 3, 7/3d, 3e types according to Fisher immunotype/O-serotype, with 3, 7, 2 and 1 types as Fisher immunotype (corresponding to 3a, 3c, 3d, 3e, 7a, 7b, 7c, 4a and 4b as O-serotype) being mainly present.

One method of treatment for *Pseudomonas aeruginosa* infections is to neutralizes the *Pseudomonas aeruginosa* toxins with antitoxins. However, the antitoxin is a therapeutic agent, which is only beneficial in patients already suffering from septicemia, and has no prophylactic effect. Further, the antitoxin recently available is very expensive and its use is limited. In addition, the most significant disadvantage accompanying the use of the antitoxin is the relatively low survival rate and the accompanying severe side effects.

One method under study to avoid the disadvantages associated with the antitoxin uses a common antigen for the prevention and treatment of *Pseudomonas aeruginosa* infections. Methods under study for obtaining the common antigen can be generally classified into two groups. The first method relates to the use of a common antigen separated and purified from *Pseudomonas aeruginosa* strains having different immunotypes as a prophylactic vaccine antigen against *Pseudomonas aeruginosa* infections [See, Japan, J. Exp. Med. 45, 355–359, 1975]. The second method relates to the use of common antigen mass produced by utilizing a genetic engineering technique in which a gene coding for the desired antigen is isolated and inserted into a suitable vector to obtain a recombinant vector and then the suitable host is transformed with the resulting recombinant vector and cultivated to express the desired antigen.

Although development of a prophylactic vaccine using a common antigen is a very effective method in theory, at present the progress of study relating to this method indicates that this method has many problems which remain unsolved. The major disadvantage is that the common antigen cannot prevent all kinds of *Pseudomonas aeruginosa* infections having different immunotypes and therefore its protective efficacy is extremely low. Such low efficacy suggests that the presence of another unknown major antigen, in addition to the common antigen, may provoke an effective prophylactic effect.

Another method for treating *Pseudomonas aeruginosa* infections is the administration of antibiotics or chemotherapeutic agents having broad-spectrum selectivity for the *Pseudomonas aeruginosa* strain. However, since there are numerous *Pseudomonas aeruginosa* strains and they generally have a very high degree of drug resistance, many patients have succumb to *Pseudomonas aeruginosa* strains which cannot be effectively treated by antibiotics.

In addition, a method using therapeutic immunoglobulin has been developed. However, such immunoglobulin exhibits no or little therapeutic effect on all *Pseudomonas aeruginosa* infections and thus has been used only for very limited types of *Pseudomonas aeruginosa* infections. This is mainly due to the immunoglobulin being prepared according to a method for preparing a polyclonal antibody to a certain microorganism and therefore cannot commonly act on the numerous *Pseudomonas aeruginosa* strains.

Attempts have been made to develop an inexpensive therapeutic agent with mouse monoclonal antibodies [See, J. Inf. Dis. 152, pp. 1290–1299, 1985] or human monoclonal antibodies [See, FEMS Microbiol. Immunol. 64, pp. 263–268, 1990] against *Pseudomonas aeruginosa.* Here, cell lines can be selected to produce the most effective neutralizing antibodies from a cell bank with cell fusion technique and then a cell line can be used as starting material to produce the desired antibody on an industrial scale. However, this method aims at the treatment of *Pseudomonas aeruginosa* infection via antibody production but not at prophylactic vaccines. In addition, this method has a disadvantage that since all infections are caused by different *Pseudomonas aeruginosa* strains with different serological and immunological types, they cannot all be treated with only one kind of monoclonal antibody. That is, monoclonal antibody therapy cannot be effectively utilized to treat all *Pseudomonas aeruginosa* infected patients.

To broaden effective treatment by this method, concurrent administration of several kinds of antibodies on the basis of their investigated cross-reactivity has been developed. Here, blood is collected from *Pseudomonas aeruginosa* infected patients and examined to identify the serological and/or immunological type of the infecting *Pseudomonas aeruginosa* strains. Then monoclonal antibodies suitable to the identified type are administered to the patient. However, this method requires a lot of time and therefore is unavailable to patient whose condition necessitates immediate treatment.

In the prior art, the use of cell wall proteins separated from *Pseudomonas aeruginosa* strains as an antigen for a vaccine has been proposed [See, Stanislavsky et al., *Vaccine*, Vol. 7, "Experimental studies on the protective efficacy of a *Pseudomonas aeruginosa* vaccine", pp. 563–565, 1989]. The Stanislavsky et al. reference describe the selection of *Pseudomonas aeruginosa* strains that can provide the cross-reactivity. Also disclosed are the toxicity and the protective immunogenicity of a protein polyvalent vaccine (PV) produced therefrom.

However, the method proposed in the above reference uses four kinds of general *Pseudomonas aeruginosa* strains, i.e. NN 170041, NN 170015, NN 868 and NN 170046, which are not attenuated and, therefore, a problem concerned with the toxicities of the *Pseudomonas aeruginosa* strains themselves is present.

In addition, the chemical composition of the vaccine according to the Stanislavsky et al appears in Table 1 on page 563. Table 1 clearly shows that the PV contains 0.06±0.02% (w/v) of LPS. It is unclear as to whether antigenicity comes from the protein or from LPS in the Stanislavsky et al vaccine. Sawada et al pointed out that the Index of Efficacy (EI) of LPS is superior by about 40–200 times to a protein [See, *J. Infect. Dis.*, Vol. 150, No. 4, pp 570–576 (1984)]. More particularly, as described in the Abstract, the amount of LPS which elicits 50% of the protective dose ($PD_{50}$) ranges 0.05–2.5 µg of Ig/mouse, while that of protein (cell wall protein) ranges between 10 and 100 µg of Ig/mouse. This means that about 40–200 times the smaller amount of LPS than the protein immunogen shows a similar protection against a *Pseudomonas aeruginosa* infection. Furthermore, even if the above amount of protein reveals $PD_{50}$, much more protein immunogen (about 200 times more than the amount of LPS content) should be administrated into a subject in order to provide a 90 to 100% protective effect.

The LPS content of 0.06±0.02% (w/v) in the Stanislavsky et al vaccine corresponds to about 900 to 1,800 ng per 1 mg of cell wall protein (CWP) when it is converted into weight (gram) units. In detail, when the protein content is 44.6% (w/v) and LPS is 0.06%, then the protein/LPS ratio is 743.3 (See, page 563, lines 7 to 11 of the Results). When LPS is 0.04%, the amount of LPS in 1 mg of CWP is 1/743.3× 0.04/0.06=897 ng. When LPS is 0.08%, the amount of LPS becomes 2 times the amount, i.e., 1794 ng. This amount is enough to elicit antigenicity.

Elin et al describe that more than 300 ng of LPS content per 1 mg of cell wall 30 protein may cause toxicities such as pyrogenic symptoms and the like [See, *J. Infect. Dis.*, 128; pp. 349–352, 1973]. More specifically, the minimal pyrogenic dose is 5 ng/kg in an endotoxin from Klebsiella as described in Table 1 at page 351; this amount corresponding to 300 ng in human (body weight of 60 kg). Thus, the LPS content of ca. 900–1800 ng in the Stanislavsky et al vaccine may cause toxic side effects when it is clinically applied to human. Moreover, Edelman et al describe that the active immunization of patients with an LPS-based *Pseudomonas aeruginosa* vaccine was not tolerated well due to adverse reactions associated with a high endotoxin content [See, page 1288, lines 2 to 5, right side column, *Vaccine*, Vol. 12, No. 4, pp. 1288–1294, (1994)].

Furthermore, Stanislavsky et al show the clinical experimental results employing the same PV in another published article [See, *Vaccine*, Vol. 9, pp 491–494, July 1991]. The PV contains 0.06±0.02% (w/v) of LPS. See, page 491, lines 13–14, right side column. Table 1 on page 493 shows that 31 volunteers (26%) among 119 volunteers have experienced febrile reactions and 48 volunteers (40.3 %) experienced systemic reactions (i.e., hyperglycemia).

It is believed that, in connection with the process for preparing the vaccine, Stanislavsky et al references employ a process in which after the cell wall of the microorganism is first disrupted, the resulting mixture is then purified by centrifugation. Stanislavsky et al disclose their process in detail in a reference [See, *Vaccine*, volume 7, pp. 562–566, December 1989]. A review of this article reveals that in the Stanislavsky et al process, the cell wall is disrupted. That is, the vaccine produced according to their process contains cytoplasmic cell components, such as, 27.2% (w/v) of nucleic acid, and 2.36% (w/v) of carbohydrates, or other components, such as 11.8% (w/v) of ash and 0.08% (w/v) of LPS in addition to 44.6% (w/v) of the target proteins.

In addition, since in preparing the above vaccine from such *Pseudomonas aeruginosa* strains, cell walls had to be destroyed to result in contamination of the medium with cytoplasmic substances such as nucleic acids and toxic high molecular substances which are present in cytoplasm, or lipopolysaccharides (LPS). These substances are then incorporated into the resulting vaccine as impurities increasing the care required in administering the vaccine and possibly restricting its use. Also, the vaccines prepared according to the conventional techniques contain a large amount of lipopolysaccharide, lipid-protein-carbohydrate component which may elicit antigenicity. Hitherto, there have not been known protein vaccines containing only cell wall proteins of *Pseudomonas aeruginosa* having molecular weight range between 10,000 and 100,000, of which antigenicity come from cell wall proteins of *Pseudomonas aeruginosa* strains, and thus can be desirably used without eliciting any side effects in the subject to be administrated.

SUMMARY OF THE INVENTION

Thus, the present inventors have extensively conducted research to find a means capable of effectively inducing antibodies against *Pseudomonas aeruginosa* which manifests good immunogenic (i.e. antigenic) activity with extremely remote risk due to inherent toxicities of *Pseudomonas aeruginosa* strains themselves. As a result, the present inventors have found that novel, safe and attenuated *Pseudomonas aeruginosa* strains, obtained by classifying *Pseudomonas aeruginosa* strains isolated from *Pseudomonas aeruginosa* infected patients into seven (7) species based on their immunotypes and then attenuating each pure strain by serial passaging the organism several times through a suitable animal host, have cell wall proteins not only which are useful in preparing a vaccine for prophylaxis against *Pseudomonas aeruginosa* infections but also which can be used as an effective antibody inducer to produce protective immunoglobulins for *Pseudomonas aeruginosa* infection in the animal body. The present inventors have also found that an immunologically effective fraction of proteins can be obtained by a process which do not involve cell wall lysis and enables to selectively obtain a specific fraction of proteins among the cell wall components. The resulting immunoglobulins exhibit superior therapeutic effect on various *Pseudomonas aeruginosa* infections, including severe cases, according to the present invention.

Therefore, it is an object of the present invention to provide a vaccine for inducing an immune response to prevent subsequent disease caused by *Pseudomonas aeruginosa* in a patient receiving the vaccine.

It is a further object of the present invention to provide a method for preparing the vaccine.

It is an another object of the present invention to provide a therapeutic agent for the treatment of *Pseudomonas aeruginosa* infection which comprises at least one immunoglobulin for *Pseudomonas aeruginosa* strain.

It is a further object of the present invention to provide a method for preparing the immunoglobulin.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the detailed description of the preferred embodiment in addition to the scope of the invention defined by the claims taken in conjunction with the accompanying drawings.

One embodiment of the present invention is directed to a novel vaccine and a process for preparing the vaccine against *Pseudomonas aeruginosa* infections. The vaccine is prepared by separating cell wall proteins in a substantially pure state from each of seven (7) types of safe attenuated *Pseudomonas aeruginosa* strains as described below and further purifying the separated cell wall proteins and then, preferably, combining the purified cell wall proteins derived from at least 3 types of attenuated *Pseudomonas aeruginosa* strains. Preferably, equivalent amounts of cell wall proteins from each of 4 types are used in preparing the vaccine according to the present invention.

The effective ingredient of the vaccine according to the present invention is a mixture of the cell wall proteins having a molecular weight of 10,000 to 100,000. These proteins are involved in structural and functional roles such as pore formation, transport of specific materials, maintenance of cell structure, and membrane stabilization [See, *Molecular Microbiol.* (1990) Vol. 4, pp. 1069–1075]. Thus, the vaccine according to the present invention is quite distinguishable from the prior art vaccines.

In the description throughout the present specification, the term "cell wall protein" refers to the protein derived from at least one of seven different Fisher-Devlin immunotypes of attenuated *Pseudomonas aeruginosa* strains, having a molecular weight of 10,000 to 100,000. This protein does not contain cytoplasmic components including alkaline protease, elastase, and exotoxin A or DNA. The protein does not also substantially contain lipopolysaccharide. Therefore, it would be understood that the term, "cell wall protein" in the specification means the protein as stated above, unless otherwise defined.

In addition, the phrase "does not substantially contain" used in the present invention in connection with the content of lipopolysaccharides of the vaccine means the amount of lipopolysaccharide which does not elicit, in a subject, any immune response by lipopolysaccharide component in a vaccine. Thus, the term "substantially no" according to the present invention means an amount below 70 ng of LPS, preferably below 50 ng of LPS, and most preferably below 1 ng of LPS per mg of protein.

Another embodiment of the present invention is directed to a therapeutic agent for *Pseudomonas aeruginosa* infection, which contains at least one immunoglobulin produced by cultivating at least one safe attenuated *Pseudomonas aeruginosa* strain, separating the cell wall protein, purifying the separated cell wall protein and then injecting the pure cell wall protein as an antibody inducer into experimental animals to induce the immunoglobulin, and a method for preparing the therapeutic agent.

The more pertinent and important features of the present invention have been outlined above to facilitate a better understanding of the detailed description of the invention which follows and so that the present contribution to the art can be fully appreciated. The features of the invention described herein form the subject of the claims of the invention. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

BRIEF DESCRIPTION OF THE DRAWINGS

For a thorough understanding of the nature and objects of the invention, reference should be had to the following detailed description taken in connection with the accompanying drawings in which.

BEST MODE FOR CARRYING OUT THE INVENTION

Fisher-Devlin Immunotypes of *Pseudomonas aeruginosa* are classified into seven types, type 1 through type 7. In the present invention, *Pseudomonas aeruginosa* strains having Fisher immunotypes 1 to 7 are selected as strains for attenuation, on the basis of the fact that they are detected in the blood of the major portion, i. e., 90 to 95% or more, of *Pseudomonas aeruginosa* infected patients. Particularly among the seven (7) types of *Pseudomonas aeruginosa*, type 1 and type 3 are the most frequently detected strains in *Pseudomonas aeruginosa* infected patients. However, the teaching of the present invention may be used against any of the strains of *Pseudomonas aeruginosa* to provide protection or treatment.

Safe attenuated *Pseudomonas aeruginosa* strains according to the present invention can be obtained by isolating each of seven types of *Pseudomonas aeruginosa* strains in a pure state from the blood of patients who are determined as having Pseudomonas aeruginosa infection and then attenuating the isolated strains with repeated purifying procedures. The safe attenuated Pseudomonas aeruginosa strains thus obtained are all seven (7) types and designated CFCPA 10142 (Fisher type 1), CFCPA 20215 (Fisher type 2), CFCPA 30720 (Fisher type 3), CFCPA 40057 (Fisher type 4), CFCPA 50243 (Fisher type 5), CFCPA 60534 (Fisher type 6) and CFCPA 70018 (Fisher type 7).

The attenuated Pseudomonas aeruginosa strains obtained by repeated purifying procedures as described above have phenotypes and microbiological properties substantially identical to those of the corresponding parent strains but show new properties useful in the preparation of a vaccine antigen for prophylaxis against Pseudomonas aeruginosa infection rather than any pathogenicity which is present in the parent strains prior to attenuation. Accordingly, the attenuated Pseudomonas aeruginosa strains according to the present invention are regarded as novel microorganism strains. Therefore, these strains were deposited at the Korean Culture Center of Microorganisms in the Korean Federation of Culture Collections, hereafter KCCM, as an international depository authority under the Budapest Treaty on May 12, 1993 under accession numbers of KCCM 10029 for CFCPA 10142, KCCM 10030 for CFCPA 20215, KCCM 10031 for CFCPA 30720, KCCM 10032 for CFCPA 40057, KCCM 10033 for CFCPA 50243, KCCM 10034 for CFCPA 60534 and KCCM 10035 for CFCPA 70018.

The purifying procedures for producing the attenuated Pseudomonas aeruginosa strains are repeatedly carried out generally until the strains show the desired $LD_{50}$ values. Although the number of purfying procedures or steps varies depending on the level of skill of the technicians, the toxicity of parent strains and the like, the purification step is preferably carried out 3 to 7 times, e.g., until the $LD_{50}$ of the Pseudomonas aeruginosa is at least $2\times10^7$ cells. The $LD_{50}$ level of novel attenuated Pseudomonas aeruginosa strains thus obtained according to the present invention in mouse is preferably $2.0\times10^7$ cells or more.

The present invention provides a vaccine for immunization against Pseudomonas aeruginosa infections which is prepared by separating cell wall proteins in a pure state from each of the novel attenuated Pseudomonas aeruginosa strains according to the present invention as obtained above and then further purifying the separated cell wall proteins, and combining the purified cell wall proteins obtained in a certain mixing ratio, preferably in equivalent amounts of the cell wall proteins from each of the desired Pseudomonas aeruginosa strain for which immunization is sought. That is, the amount used for each strain is that sufficient to induce immunization against that strain in a particular host type.

In addition, the present invention provides a method for preparing vaccines for immunization against Pseudomonas aeruginosa, comprising the steps of:

a) preparing pure isolated cells of Pseudomonas aeruginosa strains;
b) treating the microorganism cells of Pseudomonas aeruginosa with an organic solvent to inactivate the cells and remove lipid components;
c) subjecting the microorganism cells thus treated to extraction to give an extract;
d) subjecting the resulting extract to fractionization and purification by ultrafiltration and ultracentrifugation to select a specific fraction of proteins;
e) recovering the selected fraction of proteins; and
f) preparing a vaccine using the selected fraction of proteins, the improvement comprising carrying out step (c) under sufficiently mild conditions that cell wall of microorganism of Pseudomonas aeruginosa is not destroyed, thereby providing an extract which does not contain any cytoplasmic substances; and selecting in step (d) the specific fraction of protein having a molecular weight of 10,000 to 100,000 and containing substantially no lipopolysaccharide.

According to the claimed process, the microorganism cells are extracted so that the cell wall is kept intact throughout step (c). Thus, the resulting extract contains proteins originating from the cell wall of microorganism, not from cytoplasm. The cytoplasmic substances are discarded after extraction. The cell wall proteins derived from the seven (7) types of attenuated Pseudomonas aeruginosa strains are combined with each other in a suitable constitution at a desired ratio, preferably in equivalent amounts.

The method for preparing vaccines according to the present invention described above can be summarized as follows.

TABLE 1

Procedures for separating and purifying cell wall proteins from attenuated Pseudomonas aeruginosa strains and for preparing vaccines Hereinafter, the vaccine compositions of the present invention will be more specifically explained with reference to the method of preparation.

For preparing vaccines for prophylaxis against Pseudomonas aeruginosa according to the present invention, seven types of attenuated Pseudomonas aeruginosa strains, i.e. CFCPA 10142, CFCPA 20215, CFCPA 30720, CFCPA 40057, CFCPA 50243, CFCPA 60534 and CFCPA 70018 are, respectively, cultivated in a suitable-sized fermenter in the first step. As the culture medium for this purpose, tryptic soy broth, or preferably a special medium as described below, is suitable to the cultivation of *Pseudomonas aeruginosa*.

The special culture medium includes glucose (30 g/l), peptone (15 g/l), $MgSO_4$ (0.5 g/l), $CaCO_3$ (5 g/l), $KH_2PO_4$ (1 g/l), $FeSO_4$ (5 mg/l), $CuSO_4$ (5 mg/l) and $ZnSO_4$ (5 mg/l). This special medium is uniquely designed by the present inventors for the cultivation of *Pseudomonas aeruginosa* strains and is novel. Accordingly, this special medium is encompassed within the scope of the present invention. When *Pseudomonas aeruginosa* strains are grown in the special medium, the yield of the bacterial mass is at least 30% higher than the bacterial mass grown in tryptic soy broth on the basis of the weight of dry bacterial mass. Therefore, the use of such special medium is preferred.

In the bacterial mass cultivation step, the optimal culture conditions are a temperature of 37° C., aeration rate of 1 vvm (volume/volume minute) and a seed volume of 5% (v/v) of the culture medium solution; and the cultivation is carried out at the stirring rate of 100 rpm for the first 2 hours and then 200 rpm for 10 to 20 hours, preferably 12 to 16 hours.

Upon the completion of cultivation, in the second step the precipitated bacterial cells are separated from the culture solution by means of centrifugation or the like. The separated bacterial cells are treated in the third step with an organic solvent to inactivate the microorganisms and at the same time to remove the cell wall lipid components. In the third step, the organic solvent is preferably selected from the group consisting of acetone, chloroform, ethanol, butanol, and the like, with acetone being most preferable.

The fourth step comprises the extraction of cell wall proteins, i.e., 5 to 6 extractions, while the cell wall is kept intact throughout this step. For this purpose, microorganism cells are retained in a solution such as phosphate buffer solution, Tris buffer solution and the like, preferably in the phosphate buffer solution, and are acted on with a mixer or homogenizer to extract the cell wall proteins. The extraction is carried out under sufficiently mild conditions so that the cell wall of the microorganism is not destroyed, thereby providing an extract which does not contain any cytoplasmic substances. The extraction is preferably carried out by stirring at 50 to 150 rpm at 4° C. This step relies on the technical concept that an immunologically effective fraction of proteins can be obtained by starting from a raw material (i.e., extract) which does not contain any cytoplasm-derived toxic components such as alkaline protease, elastase, exotoxin A, and DNAs, thereby providing a vaccine substantially free of toxicity and having high protective efficacy. The term "cytoplasmic substances" used in the present invention was intended as contaminants which can be interchangeably used with cytoplasm-derived components. Examples of such substances include nucleic acids such as DNA, and proteins such as alkaline protease, elastase, exotoxin A, and other high-molecular substances which are present in cytoplasm. The term "sufficiently mild condition" used throughout the specification means a condition that the cell wall of a microorganism, i.e., *Pseudomonas aeruginosa* is not destroyed or lysed by any mechanical or chemical treatments of cells, while it is performed on being through a series of isolating procedure such as treatment of organic solvent and extraction of cell wall protein. During the extraction procedure, it is necessary to continuously or simultaneously inspect whether the cells are being destroyed or not by the presence of lactate dehydrogenase or hexokinase as a cytoplasmic marker enzyme. The inspection step is not essential to the procedure. The present invention uses lactate dehydrogenase as a cytoplasmic marker in order to inspect whether the cell wall was destroyed or not. This inspection is not critical but an optional step in the procedure.

Thereafter, the cell wall proteins of the attenuated *Pseudomonas aeruginosa* strains obtained in a supernatant according to above procedures are fractionized by subjecting them to the first and second ultrafiltrations to obtain only the proteins having molecular weights between 10,000 and 100,000. In this step, it is very important that a molecular weight of the resulting cell wall proteins be within the range of 10,000 to 100,000. The reason is that the molecular weight of cell wall proteins less than 10,000 does not provide the desired prophylactic effect as determined by animal experiments, while a molecular weight higher than 100,000 may cause toxic effects due to the presence of high molecular lipopolysaccharide (LPS).

The separated cell wall proteins from each of the seven types of attenuated *Pseudomonas aeruginosa* having molecular weight between 10,000 and 100,000 are each further purified by ultracentrifugation to remove any possible minor lipopolysaccharide that may be present. Then, a step to remove LPS and insoluble particles is performed to finally obtain the cell wall proteins of attenuated *Pseudomonas aeruginosa* strains which are nonpathogenic and which have sufficient purity for use as a vaccine for prophylaxis against the *Pseudomonas aeruginosa* infection.

The cell wall proteins obtained from the seven types of attenuated *Pseudomonas aeruginosa* strains are then combined at a certain ratio to formulate the vaccine. When considering the frequency of occurrence of disease of the parent *Pseudomonas aeruginosa* strains prior to attenuation, the combination of cell wall proteins should be made by mixing cell wall proteins obtained from at least three (3) types, more preferably four (4) types or more, and most preferably all of the seven (7) types of the *Pseudomonas aeruginosa* strains. Although the mixing ratio varies with the types of *Pseudomonas aeruginosa* strains from which the cell wall proteins to be combined are obtained, the cell wall proteins are preferably mixed in a ratio of equivalent amounts.

For instance, the preferred vaccine compositions according to the present invention are those containing cell wall proteins obtained from CFCPA 10142, CFCPA 20215, CFCPA 30720 and CFCPA 60534 in a mixing ratio of 1:1:1.5:0.5; 1:1:1:1 or 0.5:1.5:1.5:0.5 or a vaccine containing all cell wall proteins obtained from CFCPA 10142, CFCPA 20215, CFCPA 30720, CFCPA 40057, CFCPA 50243, CFCPA 60534 and CFCPA 70018 in a mixing ratio of substantially equivalent amounts. The least amount of cell wall protein mixture from each of the strains of *Pseudomonas aeruginosa* present in the vaccine is that minimum amount which is sufficient to induce immunization in the intended host/patient.

If desired, the vaccine for prophylaxis against *Pseudomonas aeruginosa* infection according to the present invention can include, in addition to the cell wall protein components obtained as above, pharmaceutically acceptable excipient, for example, calcium hydroxide, calcium phosphate, ISCOM (immunostimulating complex), SAF-1 (Syntex Adjuvant Formulation-1), SAFm (modified Syntex Adjuvant Formulation) and similar excipient known to those skilled in the art.

For use as a prophylactic vaccine against *Pseudomonas aeruginosa* infection, the dosage to be administered varies with sex, age, weight, health condition, and the like, of the subjects who may be exposed to *Pseudomonas aeruginosa*, but is generally 0.5 to 2.5 mg of the mixture of cell wall protein from each of the attenuated strains. This amount is generally obtained from a bacterial mass of dry weight 0.1 g to 0.5 g (corresponding to wet weight 0.5 to 2.5 g). The preferred route of administration is by intramuscular injection.

According to another aspect of the present invention, the cell wall protein obtained in a pure state from the attenuated *Pseudomonas aeruginosa* strain of the present invention can also be used as an antibody inducer to induce immunoglobulin in experimental animals. Therefore, the present invention provides a therapeutic agent for treating a *Pseudomonas aeruginosa* infection, which contains an immunoglobulin produced by injection of the cell wall protein in a pure state obtained by separation and purification as mentioned above, into an experimental animal to induce production of a protective immunoglobulin against *Pseudomonas aeruginosa* infection.

Specifically, the separated and purified cell wall protein obtained according to the procedures as specifically illustrated above, from attenuated *Pseudomonas aeruginosa* strains of the present invention is an antigen used to immunize experimental animals, such as sheep, rabbit, etc., to induce the formation of the related antibody. The blood is collected from the experimental animals and then the serum is separated. The separated serum is treated in a known manner to obtain the desired immunoglobulin in a purified state. For this purpose, the separation and purification of immunoglobulin from the separated serum can be practiced according to the method well-known in the relevant technical field [See, Practical Immunology, 3rd ed. (1989), pp. 292–294], for example, by mixing the separated serum with phosphate buffer solution, adding the mixture to DEAE-cellulose (diethylaminoethyl-cellulose) to allow the immunoglobulin to be absorbed, removing the supernatant, washing immunoglobulin-absorbed DEAE-cellulose several times with phosphate buffer solution and then eluting from immunoglobulin-absorbed DEAE-cellulose with NaCl-phosphate buffer solution to obtain the purified immunoglobulin.

The immunoglobulin as the therapeutic agent for treating *Pseudomonas aeruginosa* infection is obtained by immunizing an experimental animal with a mixture containing cell wall proteins separated from various attenuated *Pseudomonas aeruginosa* strains in a certain ratio. For this purpose, a combined immunoglobulin obtained by immunizing the experimental animal with a mixture consisting of each of cell wall proteins obtained from each of the seven (7) types of attenuated *Pseudomonas aeruginosa* strains in a certain ratio, preferably in a ratio of equivalent amounts can be used. However, when the cross reactivity of each of the immunoglobulins is considered, the immunoglobulins obtained by immunizing an experimental animal with a mixture consisting of cell wall proteins separated from each of the 4 types of attenuated *Pseudomonas aeruginosa* strains as follows: CFCPA 10142, CFCPA 20215, CFCPA 30720 and CFCPA 60534 and in a ratio of 1:1:1:1 provides considerable therapeutic effect on infections caused by all of the Pseudomonas strains having Fisher types 1, 2, 3, 4, 5, 6 and 7. This is the preferred combined immunoglobulin therapeutic agent for treating a disease caused by *Pseudomonas aeruginosa*.

The immunoglobulin for *Pseudomonas aeruginosa* according to the present invention can be formulated into pharmaceutical compositions in a lyophilized form or in a liquid form and, if necessary, additionally contain pharmaceutically acceptable carriers, for example, stabilizers, preservatives, isotonic agents, and the like. The pharmaceutically acceptable which can be used preferably include, for example, mannitol, lactose, saccharose, human albumin, the like in the case of lyophilized preparations and physiological saline, water for injection, phosphate buffer solution, aluminum hydroxide, etc. in the case of liquid preparations.

The dosage of immunoglobulin varies depending on the age, body weight, sex and general state of health of the subject, the severity of *Pseudomonas aeruginosa* infection and the components of the combined immunoglobulin being administered. The immunoglobulin is generally administered in an amount of 0.1 mg to 1000 mg, preferably 1 mg to 100 mg, per day per kg body weight to an adult via the intravenous route.

The present invention will be more specifically illustrated by the following examples but is not limited in any way to the examples.

EXAMPLE 1

Isolation of *Pseudomonas aeruginosa* strain from *Pseudomonas aeruginosa* infected patients and identification thereof From each of 260 different samples of blood taken from *Pseudomonas aeruginosa* infected patients, about 1 to 5 ml aliquot was aseptically collected and allowed to stand for one hour at room temperature. After the blood was stored overnight in a refrigerator at 4° C., it was centrifuged with 1500×g (g: gravity) for 10 minutes at 4° C. to remove the solid substances and to obtain a supernatant serum. The serum obtained above was diluted with phosphate buffer solution ($NaH_2PO_4$ 1.15 g, KCl 0.2 g , $KH_2PO_4$ 0.2 g, NaCl 8.766 g per liter) in a ratio of 1:10 (serum to solution) and then spread on a tryptic soy broth culture plate adding 1.0 to 1.5% agar, which was previously prepared. The culture plate was incubated for 12 hours, or more, in an incubator maintained at a constant temperature of 37° C. under aerobic conditions. The cultures thus obtained were transferred to fresh culture plates and then the desired microorganisms were isolated in a pure state by means of a known microorganism pure isolation method [See, Thomas D. Brock and Michael T. Madigan, Biology of Microorganisms (1988), 5th ed. pp. 32–33, Prentice Hall, Englewood Cliffs, N.J.].

For the isolated *Pseudomonas aeruginosa* strains, their serological and immunological characterizations have already been disclosed (See, Bergey's Manual) and their identification can be determined using a commercial analysis kit according to the analytical method described in *J. Gen. Microbiol*, 130, pp. 631–644, 1984. Each *Pseudomonas aeruginosa* strain was inoculated into a test tube containing 5 ml of tryptic soy broth and then cultivated at 37° C. under aerobic conditions to adjust the concentration of bacterial mass so as to maintain the absorbance of approximately 2.0 or more under visible light of 650 nm.

An aliquot of 1 ml was aseptically taken from this culture solution and centrifuged at 6000×g at 4° C. for 10 minutes. The supernatant culture solution was removed and the precipitated microorganism was suspended by adding the same amount of sterilized saline. 15 μl of each of test sera contained in the kit and control serum (normal rabbit serum) were added to each well of a 96-well microplate and were mixed with 15 μl of microorganism suspension obtained above to determine whether the agglutination occurs within 10 to 30 minutes. In this study, since the microorganism strain in a well with positive agglutination has a serotype identical with that of serum added thereto, the identification of the isolated microorganisms could be readily achieved.

EXAMPLE 2

Selection of attenuated *Pseudomonas aeruginosa* strains from each isolated *Pseudomonas aeruginosa* strains In order to attenuate *Pseudomonas aeruginosa* strains to obtain safe microorganisms for use in the preparation of a vaccine, one strain for each of the *Pseudomonas aeruginosa* strains having different immunotypes was selected and then attenuated through repeated purifications.

In this procedure, the control for a toxic *Pseudomonas aeruginosa* strain GN 11189 (Episome Institute, Japan) was selected, which shows a lethality rate of 100% within 3 days after intravenous (or intraperitoneal) injection of $2.0 \times 10^7$ cells of GN 11189 into a male ICR mouse weighing 20 to 25 g.

Each strain of the above selected *Pseudomonas aeruginosa* strains having a different immunotype was cultured in liquid tryptic soy broth under the same conditions as in Example 1 and then centrifuged with 6000×g at 4° C. for 10 minutes. The obtained cell precipitate was suspended in 10 ml of physiological saline, centrifuged again under the same conditions as above, and then diluted with fresh physiological saline to adjust the cell content to $5 \times 10^5$, $5 \times 10^6$, $5 \times 10^7$ and $5 \times 10^8$ cells per ml. Each cell dilution was administered to one group consisting of 10 ICR mice via the intravenous (or intraperitoneal) route. To the control group, the GN 11189 strain was administered in an amount of $2.0 \times 10^7$ cells per control animal. At the point where the lethality within 3 days in the control group is 100%, *Pseudomonas aeruginosa* strains were aseptically isolated from ICR mice/mouse survived at the highest cell concentration. The isolated *Pseudomonas aeruginosa* strains were spread again on tryptic soy agar plate medium. Following microorganism pure isolation method as mentioned above each microorganism strain was isolated in a pure state.

All seven (7) kinds of the first attenuated microorganisms were repeatedly passed through ICR mice about 3 to 7 times according to the method described above until the desired $LD_{50}$ of at least $2.0 \times 10^7$ cells was achieved for each microorganism strain. The safety value of each finally attenuated *Pseudomonas aeruginosa* strain, which is expressed as $LD_{50}$ is listed in Table 2.

TABLE 2

Safety values of attenuated *Pseudomonas aeruginosa* strains selected according to the present invention

|  | Selected *P. aeruginosa* strains | Fisher Immunotype | Initial $LD_{50}$ | Final $LD_{50}$ |
| --- | --- | --- | --- | --- |
| Test strain | CFCPA 10142 | 1 | <1.5 × 10⁶ | 7.6 × 10⁷ |
|  | CFCPA 20215 | 2 | <1.4 × 10⁶ | 2.7 × 10⁷ |
|  | CFCPA 30720 | 3 | <2.0 × 10⁶ | 2.5 × 10⁸ |
|  | CFCPA 40057 | 4 | <3.7 × 10⁶ | 4.5 × 10⁷ |
|  | CFCPA 50243 | 5 | <5.0 × 10⁶ | 3.0 × 10⁷ |

TABLE 2-continued

Safety values of attenuated *Pseudomonas aeruginosa* strains selected according to the present invention

|  | Selected *P. aeruginosa* strains | Fisher Immunotype | Initial $LD_{50}$ | Final $LD_{50}$ |
| --- | --- | --- | --- | --- |
|  | CFCPA 60534 | 6 | <1.5 × 10⁶ | 2.0 × 10⁷ |
|  | CFCPA 70018 | 7 | <3.8 × 10⁶ | 2.7 × 10⁷ |
| Control Strain | GN 11189 | — | — | 2.0 × 10⁶ |

All of the seven (7) kinds of microorganisms mentioned above exhibited the $LD_{50}$ value of at least $2.0 \times 10^7$ cells. Accordingly, it could be identified that the attenuated microorganisms were selected.

EXAMPLE 3

Identification of attenuated *Pseudomonas aeruginosa* strain

Sterilized cetrimide 10% (w/v) was added to a liquid nutrient medium (pH 7.2–7.4), which was prepared by steam sterilization in an autoclave at 121° C. for 15 minutes, to a final concentration of 0.3% (v/v). A 10 ml aliquot of the medium thus obtained was aseptically taken and then introduced into a test tube, to which one drop of each attenuated *Pseudomonas aeruginosa* strain isolated in a pure state according to Example 2, above, was inoculated and then subjected to seed culture at 30° to 37° C. for 12 to 16 hours. From the test tube in which the growth of microorganism occurs, 0.5 ml of the culture solution was taken, spread on a plate of cetrimide agar medium as *Pseudomonas aeruginosa* isolation medium and then the plate was incubated. The colony first identified as *Pseudomonas aeruginosa* by pigment formation was transferred and incubated on a *Pseudomonas aeruginosa* agar medium for detection of fluorescin (Proteose peptone No. 3 (oxoid) 2%, Glycerol (bidistilled) 1%, $K_2HPO_4$ (anhydrous) 0.15%, $MgSO_4 \cdot 7H_2O$ 0.15%, Agar 1.5% (w/v), pH 7.2) and then a *Pseudomonas aeruginosa* agar medium for detection of pyocyanin (Peptone (Difco) 2%, Glycerol (bidistilled) 1%, $K_2SO_4$ (anhydrous) 1%, $MgCl_2$ (anhydrous) 0.14%, Agar 1.5% (w/v), pH 7.2) and then examined again for morphological test, nutritional requirement and oxidase test to determine the presence of the *Pseudomonas aeruginosa* strain. The types of the selected *Pseudomonas aeruginosa* strains were determined according to the IATS classification system by using a *Pseudomonas aeruginosa* antigen kit (produced by Difco Laboratories, Detroit, Mich., USA) and then classified by Fisher immunotype. The results thereof are described in Table 3.

TABLE 3

Criteria for selection of *Pseudomonas aeruginosa* strains and their serotype and protective range

| Test item | Test Results |
| --- | --- |
| Growth on isolation medium | Growth |
| Growth on *Pseudomonas aeruginosa* medium for detection | Growth |
| Morphological features (Microscope) | Both ends are round and a single polar flagellum is present. |
| Gram Staining | Gram negative |
| Oxidase reaction | Positive response(+) or positive-negative response(±) |

TABLE 3-continued

Criteria for selection of *Pseudomonas aeruginosa* strains and their serotype and protective range

| Test item | Test Results |
| --- | --- |
| Antigen-Antibody reaction (first selected strains) | |
| CFCPA 20215 | Protective for Fisher types 3 and 7 as Fisher inununotype 2 (Lanyi O-serotype 7) |
| CFCPA 60534 | Protective for Fisher types 3 and 7 as Fisher immunotype 6 (Lanyi O-serotype 5) |
| CFCPA 10142 | Protective for Fisher types 2 and 1 as Fisher immunotype 1 (Lanyi O-serotype 4) |
| CFCPA 30720, CFCPA 30721 | Protective for Fisher type 6 as Fisher immunotype 3 (Lanyi O-serotype 3) |

EXAMPLE 4
Physiological characteristics of attenuated *Pseudomonas aeruginosa* strains (1) Each of the seven kinds of *Pseudomonas aeruginosa* strains attenuated according to Example 2, growth rates depending on different pH values were determined. Each microorganism strain was inoculated into 50 ml of tryptic soy broth with a pH value of 7.2, and then pre-incubated at 37° C. for 12 to 16 hours under aerobic conditions with the agitation rate of 200 rpm. Each pre-incubated bacterial mass strain was inoculated into 500 ml of each of fresh tryptic soy broth of pH 3.0, pH 5.0, pH 7.0 and pH 9.0 in the final concentration of 1% (v/v) and then cultivated in fermenters at 37° C. under the same conditions as above. During this period, a sample was obtained from each culture medium at an interval of 2 hours and then the concentration of bacterial mass was determined by measuring the absorbance of the sample at 600 nm by means of spectrophotometer. The results thereof are described in Table 4.

TABLE 4

Microorganism growth rates depending on pH value

| Strains | pH 3.0 | pH 5.0 | pH 7.0 | pH 9.0 |
| --- | --- | --- | --- | --- |
| CFCPA 10142 | − | +++ | +++ | +++ |
| CFCPA 20215 | − | +++ | +++ | +++ |
| CFCPA 30720 | − | +++ | +++ | ++ |
| CFCPA 40057 | − | +++ | +++ | ++ |
| CFCPA 50243 | − | +++ | +++ | ++ |
| CFCPA 60534 | − | +++ | +++ | ++ |
| CFCPA 70018 | − | +++ | +++ | +++ |

Note:
+ Growth,
− No growth

As can be seen from Table 4, the attenuated *Pseudomonas aeruginosa* strains according to the present invention did not grow under excessively acidic conditions, for example at pH 3.0, but showed substantially identical or similar growth rates under medium conditions at pH 5.0 to pH 9.0. Therefore, in the present invention all 7 kinds of microorganisms can grow very well within a wide pH range.

(2) According to the same method as in (1), above, the growth rates of *Pseudomonas aeruginosa* strains were determined according to temperature variations. Each of the 7 kinds of attenuated *Pseudomonas aeruginosa* strains was inoculated into 50 ml of tryptic soy broth at a pH value of 7.0 and then preincubated for 12 to 16 hours at 37° C. under aerobic conditions with the agitation rate of 200 rpm. Each of the pre-incubated strains was inoculated into 500 ml of tryptic soy broth at a pH value of 7.0 and then cultivated in fermenters, which were maintained at different temperatures of 25° C., 30° C., 37° C. and 42° C., under the same conditions as above. During this period, the growth rate in each fermenter was determined by measuring the absorbance of the culture solution at 600 nm by means of spectrophotometer. The results are described in Table 5.

TABLE 5

Microorganism growth rates depending on temperature variations

| Strains | 25° C. | 30° C. | 37° C. | 42° C. |
| --- | --- | --- | --- | --- |
| CFCPA 10142 | + | +++ | +++ | + |
| CFCPA 20215 | + | +++ | +++ | + |
| CFCPA 30720 | ++ | +++ | +++ | + |
| CFCPA 40057 | + | ++ | +++ | + |
| CFCPA 50243 | + | ++ | +++ | + |
| CFCPA 60534 | ++ | +++ | +++ | + |
| CFCPA 70018 | + | ++ | +++ | + |

Note:
+ Growth,
− No growth

As seen from Table 5, all 7 kinds of attenuated *Pseudomonas aeruginosa* strains showed the best growth at 37° C. and also showed the good growth at 30° C., 25° C. However, at 42° C. each of the seven kinds of *Pseudomonas aeruginosa* strains showed a relatively slow growth rate relative to the growth rate at the other temperatures.

(3) The following experiment was to determine the effect of carbon source on the growth rate of attenuated *Pseudomonas aeruginosa* strains. Each of the 7 kinds of attenuated *Pseudomonas aeruginosa* strains was inoculated into 50 ml of tryptic soy broth at a pH value of 7.0 and then incubated at 37° C. for 12 to 16 hours under aerobic conditions with the agitation rate of 200 rpm. The culture medium was then centrifuged with 6000×g at 4° C. for 10 minutes under aseptic conditions to harvest the bacterial mass which was then resuspended in 10 ml of physiological saline. Each 50 $\mu$l of the microorganism suspensions obtained above was, respectively, inoculated to 5 ml of M9 medium ($Na_2HPO_4 \cdot 7H_2O$ 12.8 g, $KH_2PO_4$ 3 g, NaCl 0.5 g, $NH_4Cl$ 1 g) containing different carbon sources (as see below) and then cultivated for 12 hours. Then, for each culture solution the extent of microorganism growth was determined by measuring the absorbance at 600 nm.

TABLE 6

Growth characteristics of attenuated Pseudomonas aeruginosa strains depending on carbon source

| carbon source | P. aeruginosa strain | | | | | | |
|---|---|---|---|---|---|---|---|
| | CFCPA 10142 | CFCPA 20215 | CFCPA 30720 | CFCPA 40057 | CFCPA 50243 | CFCPA 60534 | CFCPA 70018 |
| Glucose | +++ | +++ | +++ | +++ | +++ | +++ | +++ |
| Xylose | − | − | − | − | − | − | − |
| Mannitol | ++ | ++ | ++ | ++ | ++ | ++ | ++ |
| Galactose | − | − | + | − | + | − | − |
| Sorbitol | − | − | − | − | − | − | − |
| Inositol | − | − | − | − | − | − | − |
| Maltose | − | − | − | − | − | − | − |
| Sucrose | − | − | − | − | − | − | − |
| Arabinose | − | − | − | − | − | − | − |
| Mannose | − | + | + | − | + | + | − |
| β-Alanine | +++ | ++ | ++ | ++ | +++ | +++ | ++ |
| Salts alone | − | − | − | − | − | − | − |

Note:
+ Growth,
− No growth

Growth characteristics of attenuated *Pseudomonas aeruginosa* strains depending on carbon sources exhibited a pattern substantially similar to the growth characteristics of general *Pseudomonas aeruginosa* strains depending on carbon sources (See, the Bergey's Manual). However, it should be noted that even though *Pseudomonas aeruginosa* has been reported as generally not using mannose, attenuated *Pseudomonas aeruginosa* according to the present invention exhibited some growth in the mannose-containing medium.

As can be seen from the above, attenuated *Pseudomonas aeruginosa* strains according to the present invention can be cultivated in a conventional medium containing a carbon source, nitrogen source, inorganic compounds, amino acids, vitamins and other nutrients under aerobic conditions at selected temperature, pH, and the like, to obtain a bacterial mass. Cell wall proteins from the resulting bacterial mass are used for preparation of *Pseudomonas aeruginosa* vaccines.

As the carbon source for cultivation of attenuated *Pseudomonas aeruginosa* strains, various carbohydrates such as glucose, mannitol, fructose, and the like, various organic acids such as acetic acid, pyruvic acid, lactic acid, and the like, can be used. For the nitrogen source, various organic and inorganic ammonium salts, peptone, yeast extracts, casein hydrolysates and the other nitrogen-containing substances can be used. As inorganic compounds, magnesium sulfate, calcium carbonate, ferrous sulfate, cuprous sulfate, zinc sulfate and potassium hydrogen phosphate and potassium dihydrogen phosphate and the like can be used. The cultivation is preferably carried out at 25° to 37° C. under aerobic conditions, for example, by means of a plate culture or of a liquid culture such as a shaking culture or aeration spinner culture. The pH value of the medium is preferably maintained at pH 5 to 9 during the period of cultivation. Preferably, the bacterial mass obtained by centrifugation of the culture solution incubated for 12 to 16 hours is used as starting material for preparation of vaccines as described hereinafter.

EXAMPLE 5

Cultivation of attenuated *Pseudomonas aeruginosa* strains (1) In a 5 L fermenter, the bacterial mass of *Pseudomonas aeruginosa* obtained according to Example 2 was cultivated for mass production, as follows: 2.5 L of the medium solution obtained by dissolving 30 g of tryptic soy broth per 1 L of distilled water was adjusted to pH 7.2, sterilized and then introduced into the 5 L fermenter. The cultivation conditions were a cultivation temperature of 37° C.; aeration rate of 1 vvm; inoculation amount of 5% (v/v) of attenuated *Pseudomonas aeruginosa* bacterial mass obtained from Example 2 for culture solution; and the agitation rate was maintained at 100 rpm for the initial 2 hours and, thereafter, the cultivation was continued for 12 to 16 hours at the fixed agitation rate of 200 rpm. Although the amounts of obtained bacterial mass were somewhat different depending on the type of the *Pseudomonas aeruginosa* strain, the average yield was approximately 8 g (dry weight) of bacterial mass per liter of culture solution.

(2) Each of the seven types of attenuated *Pseudomonas aeruginosa* strains was cultivated under the same culture conditions as in the above (1), except that the special medium for culturing *Pseudomonas aeruginosa* which consists of glucose (30 g/1), peptone (15 g/1), $MgSO_4$ (0.5 g/1), $CaCO_3$ (5 g/1), $KH_2PO_4$ (1 g/1), $FeSO_4$ (5 mg/1), $CuSO_4$ (5 mg/1) and $ZnSO_4$ (5 mg/1), is used as a medium. With this special medium approximately 10.4 g to 10.5 g (dry weight) of bacterial mass for each microorganism strain was obtained. Thus, the use of this special medium can provide the yield of bacterial mass which is at least 30% (based on dry weight) higher than that in tryptic soy broth.

EXAMPLE 6

Partial purification of a cell wall protein from attenuated *Pseudomonas aeruginosa* strains For preparing vaccines against *Pseudomonas aeruginosa*, cell wall proteins from each of the seven kinds of attenuated *Pseudomonas aeruginosa* strains were partially purified. Hereinafter, the type 3 strain, i.e. CFCPA 30720(KCCM 10031), is used as a typical example. However, the other attenuated *Pseudomonas aeruginosa* strains can also be subjected to the same method as the following purification method to obtain the partially purified cell wall proteins.

2.5 L of the special medium as used in Example 5 (2) above was introduced into a 5 L fermenter and then cultivated for 12 to 16 hours while maintaining the same culture conditions as above. Upon the completion of cultivation, 2.5 L of the culture solution was centrifuged with 6000×g at 4°

C. for 20 minutes to remove the supernatant. The precipitated cells were resuspended in a phosphate buffer solution (Na$_2$HPO$_4$ 1.15 g, KCl 0.2 g, KH$_2$PO$_4$ 0.2 g, NaCl 8.766 g, per liter, pH 7.2) at 4° C., centrifuged again and then washed with the same phosphate buffer solution. To 130 g of the cells thus obtained was added 3 volumes (about 390 ml) of acetone with respect to the original wet cell volume and the mixture was allowed to stand at 4° C. for 12 hours or more. The acetone was removed from the precipitated cell and 2 volumes (about 260 ml) of fresh acetone with respect to the original wet cell volume was added again to the residue. The resulting mixture was stirred for 5 to 10 minutes and then centrifuge at 8000×g at 4° C. for 20 minutes. The supernatant acetone was removed and the same volume of acetone was added to the residue. The mixture was stirred and centrifuged according to the same manner described above to remove the supernatant. The precipitated cells were allowed to stand at room temperature to remove acetone. The microorganism were resuspended by adding 250 ml of the same phosphate buffer solution as above so that the final concentration can be adjusted to 10% (v/v). The resulting mixture was treated with a homogenizer at the rate of 50 to 150 rpm for 10 minutes while maintaining the temperature of 4° C. to extract cell wall proteins. The suspension was centrifuged with 8000 to 10000×g for 30 minutes to obtain the supernatant. The precipitated cells were separated, suspended again by adding the same volume of phosphate buffer solution and then subjected to a second extraction under the same conditions as the above first extraction to obtain the supernatant.

By using the same conditions as the first extraction method, the cell wall proteins were repeatedly extracted 5 to 6 times while taking care to not destroy (lyse) any of the cells. The destruction of the cells can be determined by measuring a specific protein as a cytoplasmic marker substance, i.e., lactate dehydrogenase or hexokinase. The extracted supernatants, each of which is tested to ensure that the cell wall proteins are extracted without the incorporation of cytoplasmic proteins, lactate dehydrogenase and hexokinase, were collected, stirred and then finally recentrifuged at 10000×g at 4° C. for 30 minutes to obtain a clear supernatant. The protein solution thus obtained was composed only of substantially pure cell wall proteins and was adjusted with protein quantitative assay so that the protein concentration is maintained at the level of 1 mg/ml to 2 mg/ml. Further, the purity of the protein solution was determined by means of 10 to 15% concentration gradient electrophoresis. As a result, it could be identified that the desired cell wall proteins having the molecular weight ranging from 10,000 to 100,000 were present (See, FIG. 1).

EXAMPLE 7

Purification of crude proteins

The following process was carried out so that the crude cell wall protein solution in the concentration of 1 to 2 mg/ml would be purified in order to contain only the effective components.

2 to 2.5 L of crude cell wall protein solution was first subjected to a molecular weight 100,000 cut-off membrane filter in the Pellicon Cassette System to remove protein and LPS molecules having molecular weight over 100,000. According to this process, proteins having molecular weight below 100,000 were recovered as filtrate and proteins and LPS having a molecular weight greater than 100,000 were continuously circulated to be separated from the protein with a molecular weight below 100,000.

As a result, the protein solution was concentrated by 10 to 20% of the initial volume and was successively washed with 20 to 25 L (ten times amount of the initial volume of protein solution) of sterilized phosphate buffer solution (Na$_2$HPO$_4$ 1.15 g, KCl 0.2 g, KH$_2$PO$_4$ 0.2 g, NaCl 8.766 g, per liter) to recover 90% or more of the proteins having molecular weight below 100,000. The proteins having molecular weight below 100,000 separated as the filtrate were applied to a molecular weight 10,000 cut-off membrane filter in the same system to remove proteins having molecular weight less than 10,000 and other impurities and at the same time to concentrate the proteins having molecular weight of 10,000 to 100,000 to a concentration of 1 mg/ml.

The supernatant thus obtained was ultracentrifuged to remove lipopolysaccharide (LPS) and cell wall-related fragments, which are possibly present in the supernatant in a trace amount. Ultracentrifugation is carried out at 180,000×g to 200,000×g for 3 hours at 4° C. After removing the precipitates, the amount of LPS was determined on separated supernatant by the LAL assay which will be illustrated below. After the first ultracentrifugation, the level of LPS showed approximately 50 ng or less per 1 mg of purified cell wall protein.

Figure 2:
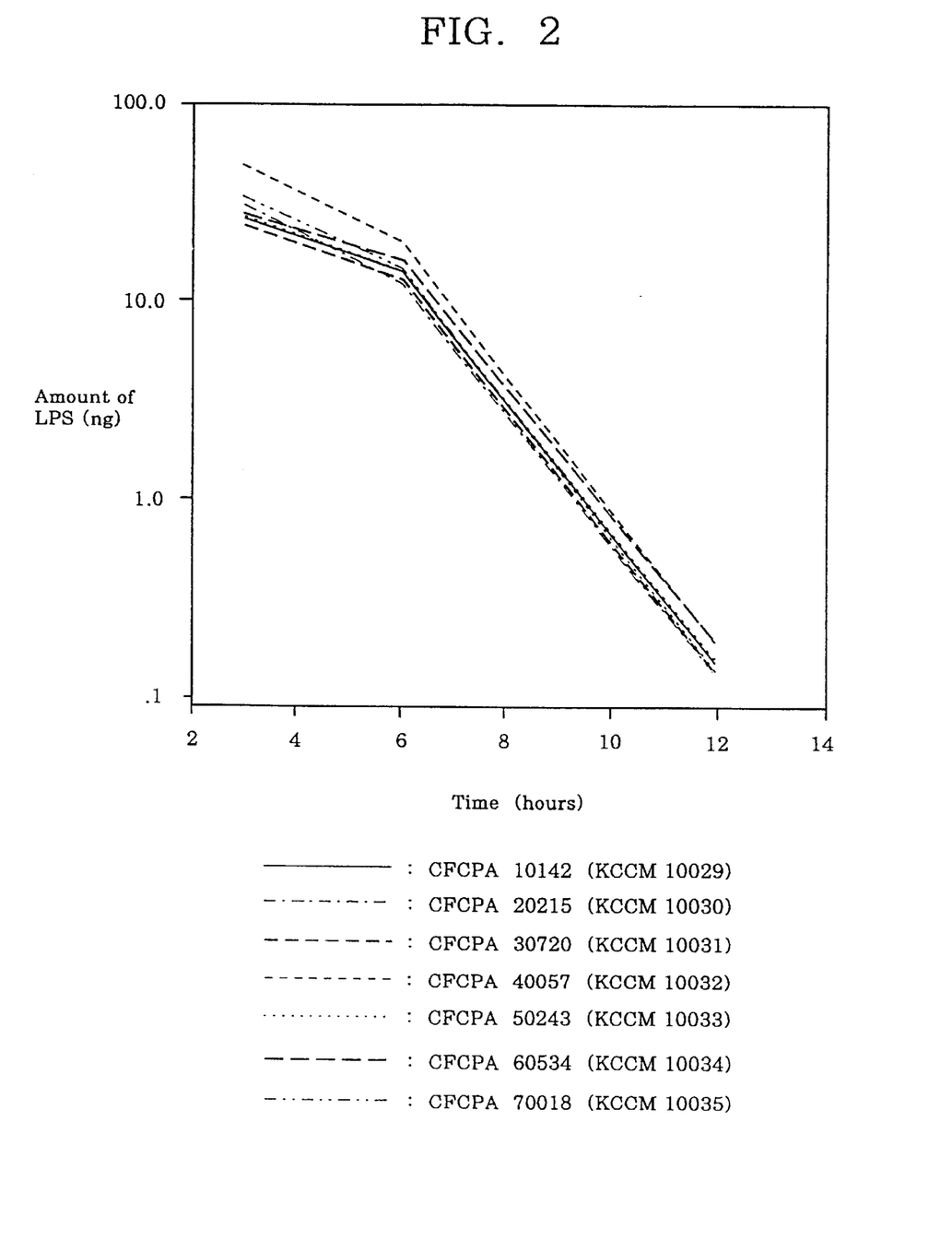
FIG. 2 is a graph representing the reduction of LPS content in cell wall protein of attenuated *Pseudomonas aeruginosa* strains depending on ultracentrifugation time.

To make a LPS-free cell wall protein based vaccine for a human use, it was re-centrifuged to completely remove LPS from the supernatant obtained above. The second centrifugation is applied for 12 hours with 180,000 g to 200,000 g at 4° C. FIG. 2 shows that the LPS content in cell wall protein of attenuated *Pseudomonas aeruginosa* strains was reduced depending on ultracentrifugation time. In this step, the inventors confirmed that the amount of LPS determined by the LAL assay was distributed to 0.1–0.2 ng range per 1 mg of cell wall protein for all seven different Fisher-immunotypes.

The final supernatant was sterilized by filtration through 0.2 μm filter to obtain 250 to 260 mg of protein composition for use in vaccines for prophylaxis against *Pseudomonas aeruginosa* infection.

EXAMPLE 8

Figure 1:
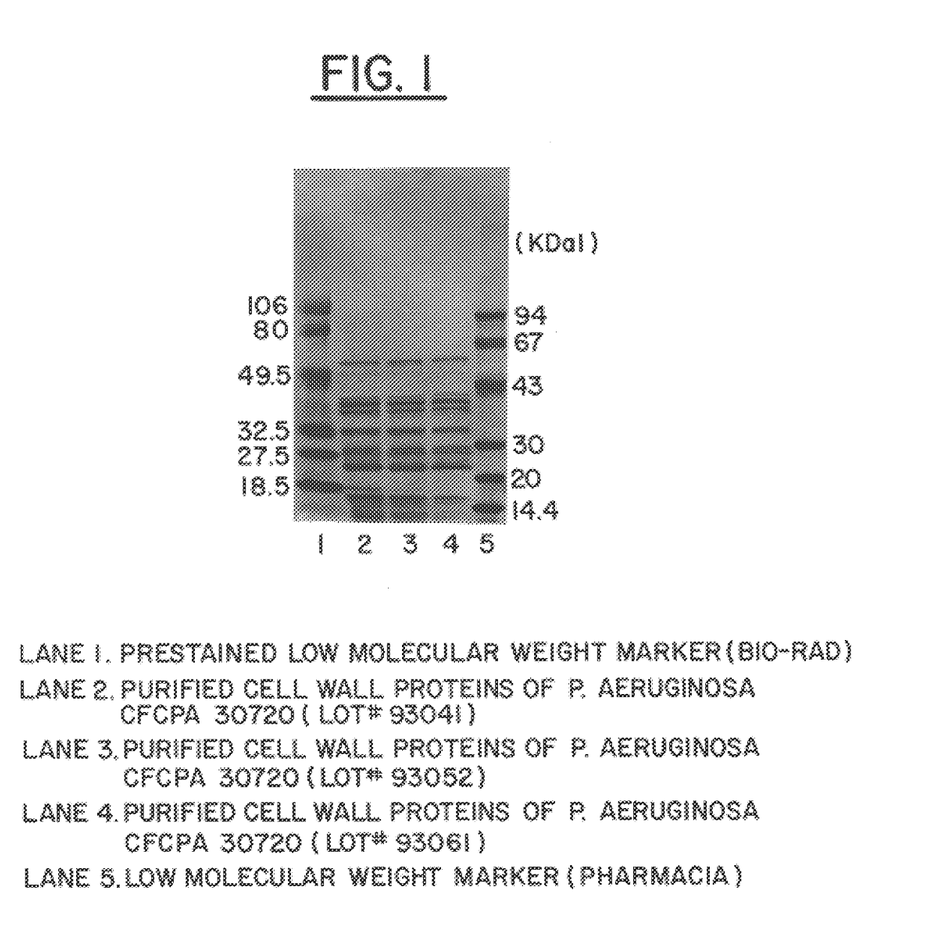
FIG. 1 shows the result of SDS-PAGE of purified cell wall proteins separated from attenuated *Pseudomonas aeruginosa* strains according to the present invention.

Purification of cell wall proteins from attenuated *Pseudomonas aeruginosa* strains having different immunotypes The remaining six kinds of attenuated *Pseudomonas aeruginosa* strains according to the present invention, i.e., CFCPA 10142, CFCPA 20215, CFCPA 40057, CFCPA 50243, CFCPA 60534 and CFCPA 70018 were treated according to the same method for microorganism cultivation and purification to prepare vaccine compositions for CFCPA 30720 *Pseudomonas aeruginosa* strain as described in Examples 5 to 7. The final *Pseudomonas aeruginosa* vaccine compositions thus obtained showed the same band pattern as CFCPA 30720 vaccine composition, in 10 to 15% concentration gradient SDS-PAGE. In addition, as a result of comparison with a standard molecular weight marker, it could be determined that all proteins contained in vaccine compositions have the molecular weight ranging from 10,000 to 100,000 (FIG. 1).

EXAMPLE 9

Quantification of a cell wall protein

In order to test the presence of the contaminants, i.e., cytoplasmic components or LPS in the cell wall protein obtained in Examples 7 and 8, the following biochemical analyses were performed on each sample.

The protein content of the separated cell wall protein from each strain was measured by the method of Lawry et al. [J. B. C. (1951) Vol. 193, pp. 265–275]. Then, the total LPS content in 1 mg of cell wall protein was measured by LAL method [Limulus Amebocyte Lysate, QCL-1000, BioWhittaker, Inc., Catalog Number 50-647U, Walkersville, Md. 21793]. The results are set forth in Table 7 below.

TABLE 7

Quantification of LPS by LAL Test

| Strain | OD at 405 nm (5 × dilution) | LPS content EU/mg p. | LPS content pg/mg p. |
|---|---|---|---|
| CFCPA 10142 | 0.147 | 0.94 | 145 |
| CFCPA 20215 | 0.188 | 1.21 | 187 |
| CFCPA 30720 | 0.125 | 0.80 | 123 |
| CFCPA 40057 | 0.19 | 1.23 | 189 |
| CFCPA 50243 | 0.158 | 1.02 | 156 |
| CFCPA 60534 | 0.129 | 0.82 | 127 |
| CFCPA 70018 | 0.133 | 0.85 | 131 |

The LAL test results revealed 0.2 ng or less of LPS content and the protein /LPS ratio was approximately $5 \times 10^6 - 1\,10^7$. It is believed that 0.2 ng or less amount of LPS per 1 mg of cell wall protein cannot elicit any toxicities such as systemic or local adverse effects in an animal model system.

For DNA analysis, agarose gel electrophoresis method was used [See, *Gel Electrophoresis of Nucleic Acids, A practical Approach*, 2nd ed., Edited by D. Rickwood et al., IRL Press, Oxford University Press, pp. 51–59 (1990)]. For a carbohydrate analysis, periodic acid staining (PAS) method was used [See, *Methods in Enzymology, Vol. 182, Guide to Protein Purification*, edited by Murray P. Deutscher, Academic Press, Inc., San Diego, Calif., p.536]. Results of the chemical composition of the cell wall protein prepared from the attenuated *Pseudomonas aeruginosa* strains are shown in Table 8.

TABLE 8

Chemical composition of cell wall protein prepared from the attenuated *Pseudomonas aeruginosa* strains

| Component | Content |
|---|---|
| Cell wall protein | 1 mg |
| Carbohydrate | ND |
| DNA | ND |
| LPS | Trace amount (< 0.2 ng) |

ND: Not detectable

As can be seen from the above tables, the LPS was present in a trace amount, i. e., below 0.2 ng per mg of the cell wall protein and it was impossible to detect other contaminants in the cell wall protein with the present analytical technique and equipment.

EXAMPLE 10
Cross-protective efficacy test with combined antigens

The cell wall proteins derived from each attenuated *Pseudomonas aeruginosa* strain after the separation and purification steps according to the methods described in Examples 7 and 8 were intraperitoneally administered in an amount of 0.2 mg/kg to 6 weeks-old ICR male mice weighing 23 to 25 g to immunize the animal. Each group consisted of 10 to 15 test animals. One week from the immunization, blood was taken from 2 to 3 mice per group for ELISA (Enzyme-linked immunosorbent assay). For the remaining ICR mice, wild-type *Pseudomonas aeruginosa* strain corresponding to the respective immunotype was injected in an amount of 10 to 50 times the initial $LD_{50}$ value for each microorganism strain listed in Table 2 of Example 2. The protective efficacy against each *Pseudomonas aeruginosa* strain was continuously examined for one week. As a result, all the test groups showed a protective effect against the corresponding *Pseudomonas aeruginosa* strains and the ELISA to all the collected blood also exhibited good positive values, which mean an improvement in the immunological responses.

In the present invention for preparing vaccines capable of exhibiting the common protective effect against infections caused by any type of *Pseudomonas aeruginosa* strains, four types of attenuated *Pseudomonas aeruginosa* strains (three types of *Pseudomonas aeruginosa* strains which are most frequently detected in human body infections and one type of *Pseudomonas aeruginosa* strain which is difficult to overcome if contracted, i.e., CFCPA 10142, CFCPA 20215, CFCPA 30720 and CFCPA 60534) were treated to obtain cell wall proteins which were combined at a ratio of equivalent amounts and then were examined for cross protective efficacy against each immunotype of *Pseudomonas aeruginosa* strains.

Cell wall proteins separated from the four types of attenuated *Pseudomonas aeruginosa* strains, as stated above, were combined at a ratio of equivalent amounts (1:1:1:1) based on protein concentration. The combined cell wall proteins were intraperitoneally administered to ICR male mice to immunize the test animals. The control group was given 0.3 ml of phosphate buffer solution ($Na_2HPO_4$ 1.15 g, KCl 0.2 g, $KH_2PO_4$ 0.2 g, NaCl 8.766 g, per liter). One week after immunization, each mouse of the test group immunized with *Pseudomonas aeruginosa* vaccine and the control group immunized with phosphate buffer solution was intraperitoneally given *Pseudomonas aeruginosa* in five (5) different concentrations diluted in a series of 10 times from $1 \times 10^8$ cells to $1 \times 10^4$ cells, and after one week, the survival number of test animals was counted to calculate the index of efficacy (EI). The results thereof are listed in Table 9, below, in which the index of efficacy is defined as a value of $LD_{50}$ in the test group divided by the $LD_{50}$ in the control group. As can be seen from Table 9, a vaccine consisting of cell wall proteins obtained from 4 kinds of attenuated *Pseudomonas aeruginosa* strains, i.e., CFCPA 10142, CFCPA 20215, CFCPA 30720 and CFCPA 60534 has an EI value of 3.0 to 18 or more against each immunotype of *Pseudomonas aeruginosa* strains. Therefore, when considering that vaccines having the EI value of at least 2 are regarded as having a good immunological effect, it can be seen that the vaccine according to the present invention shows a good protective effect against infections caused by any type of the 7 kinds of *Pseudomonas aeruginosa* strains.

TABLE 9

Cross-protective efficacy test for *Pseudomonas aeruginosa* vaccine prepared using four (4) different species of attenuated *Pseudomonas aeruginosa* strains against each type of microorganisms

| Challenge Strain | Fisher-Immunotype | Habs-Serotype | EI value |
|---|---|---|---|
| Parent strain of CFCPA 10142 | 1 | 06 | 9.5 |
| Parent strain of CFCPA 20215 | 2 | 011 | 13 |
| Parent strain of CFCPA 30720 | 3 | 02 | >18 |
| Parent strain of CFCPA 40057 | 4 | 01 | 3 |
| Parent strain of CFCPA 50243 | 5 | 010 | 4.5 |
| Parent strain of CFCPA 60534 | 6 | 07 | 8.4 |
| Parent strain of CFCPA 70018 | 7 | 05 | 7 |

According to the procedure mentioned above, except that the mixture of cell wall proteins prepared were derived from 3 types of attenuated *Pseudomonas aeruginosa* strains, CFCPA 10142, CFCPA 30720 and CFCPA 20215 (Group I), and the mixture of cell wall proteins prepared from all 7 types of attenuated *Pseudomonas aeruginosa* strains (Group II), wherein all the cell wall proteins are present in a ratio of equivalent amounts, are used instead of the mixture of 4 kinds of proteins, the cross-protective efficacy of these 2 kinds of vaccines against infection of each *Pseudomonas aeruginosa* was examined. The results are described in Table 10.

TABLE 10

Cross-protective efficacy test for vaccines originated from 3 types (Group I) or 7 types (Group II) of attenuated *Pseudomonas aeruginosa* strains against each type of microorganism

| Challenge Strain | ($LD_{50}$ in test group EI Value (——————) $LD_{50}$ in control group) | |
|---|---|---|
|  | Group I | Group II |
| Parent strain of CFCPA 10142 | 14.3 | 9.2 |
| Parent strain of CFCPA 20215 | 12.0 | 10.7 |
| Parent strain of CFCPA 30720 | >18.0 | 15.0 |
| Parent strain of CFCPA 40057 | 2.5 | 8.3 |
| Parent strain of CFCPA 50243 | 4.0 | 10.6 |
| Parent strain of CFCPA 60534 | 3.7 | 9.7 |
| Parent strain of CFCPA 70018 | 2.8 | 12.9 |

As can be seen from the above experimental results above, this vaccine shows excellent protective effect against any immunotype of *Pseudomonas aeruginosa* in comparison with only one kind of common antigen since the mixed protein components vaccine according to the present invention is composed of cell wall proteins prepared from at least three (3) different kinds of attenuated *Pseudomonas aeruginosa* strains showing different immunotypes from each other. That is, although the efficacy index of the vaccine according to the present invention varies with the kind and the number of microorganisms selected from attenuated *Pseudomonas aeruginosa* strains, the mixing ratio of the cell wall proteins derived therefrom, immunological schedule and method, and the like, it can be confirmed that the vaccine of the present invention is effective against all *Pseudomonas aeruginosa* strains presently occurring in hospitals and patients.

EXAMPLE 11
Determination of protective efficiency of the combined antigen in a rabbit model
In order to determine protective efficacy of the combined antigen against *Pseudomonas aeruginosa* pulmonary infection in rabbits, cell wall protein antigen prepared from 4 kinds of different strains (CFCPA 10142, CFCPA 20215, CFCPA 30720, and CFCPA 60534) according to the methods described in Examples 7 and 8 were diluted to a concentration of 1.0 mg/ml. One day before the test, *Pseudomonas aeruginosa* GN11189 was cultivated with vigorous shaking in tryptic soy broth (Difco Co.) for 18 hours at 37° C. and the optical density of spectrophotometer (Milton Ray Co. USA) at 600 nm was adjusted to 0.6. The obtained culture broth was suspended with gastric mucin to enhance the survival rate of challenge strain in animal. At the same time, in order to determine the bacterial administration concentration, bacterial suspension was serially diluted and incubated in an agar plate. Japanese white rabbits (male, 1.8–2.3 kg) were divided into 3 groups, each group consisting of 10 animals. The group I rabbits were intramuscularly administered an amount of 0.5 mg/kg/ml of the combined antigen a total of 3 times at the interval of 2 days to immunize the animal. Control groups II and III were administered equal amount of saline as the same manner in group I. Seven days after the last combined antigen was administrated, rabbits of group I and II were intraperitoneally administered an amount of 125 mg/kg of katamine to anesthetize the animals. To the rabbit were injected 100 µl of the prepared bacteria to induce a respiratory infection model. Rabbits of negative control group III were administered an equal amount of saline in the same manner. After lapse of 48 hours, rabbits were sacrificed. The lung was separated and weighted. The lung was added to 10 volumes of saline depending on its weight (for example, 270 ml of saline is added if the weight of lung is 30 g) and homogenized for 10 second with a blade type homogenizer (Brinkmann Co.). The resulting solution was diluted with 100× and 10,000×. 100 µl of each homogenized cell solution was positioned in a petri dish, and BET lactose agar was added thereto. The mixture was then incubated overnight to count the number of live colonies (blue color). The results of this test are shown in Table 11 below.

TABLE 11

Protective effect of combined cell wall protein against *Pseudomonas aeruginosa* pulmonary infection in rabbit

| Group | Dosage mg/kg/ml | immunization-challenge period (days) | immunization-challenge challenge (cfu) | challenge-sacrifice interval (days) | No. of isolated interval (days) | P. aeruginosa |
|---|---|---|---|---|---|---|
| I (Vaccinated group) | 0.5 | 2 | $5.3 \times 10^4$ | 7 | 2 | $1.7 \times 10^2$ |
| II (Positive group) | Saline | 2 | $5.3 \times 10^4$ | 7 | 2 | $9.6 \times 10^3$ |
| III (Negative Group) | Saline | 2 | Saline | 7 | 2 | $1.2 \times 10$ |

As can be seen from the above table, the test results show that the combined antigen (group I) revealed the reduction in the number of live colonies by 56 times as compared with positive control group and 97% or more of reduction as compared with the first administered bacteria. It was confirmed that the antigen has a significance in the respiratory infection rabbit model.

EXAMPLE 12
Toxicological test for cell wall proteins

To prepare a component vaccine for prophylaxis against infection caused by *Pseudomonas aeruginosa,* the safety of cell wall proteins themselves to be used as component vaccine as well as the safety of microorganism strains themselves as described in Example 2 should be assured. In this example, cell wall proteins were partially purified and then examined for their safety in experimental animals, i.e., mouse, rat, and beagle dog. Specifically, each attenuated microorganism was cultivated with tryptic soy broth as the culture medium, in a 5 L fermenter and then treated according to the procedures described in Examples 5, 6 and 7. The supernatants of the cell wall proteins extracted from attenuated *Pseudomonas aeruginosa* strains were collected together, centrifuged again with 10000×g at 4° C. for 30 minutes to remove fine particles possibly present in solution. The resulting cell wall proteins were filtered through an Amicon membrane filter to obtain a mixture of cell wall proteins having molecular weight ranging from 10,000 to 100,000, which was concentrated to a protein concentration of 1 mg/ml and then sterilized with a 0.2 $\mu$ filter to obtain a protein source for toxicological testing.

(1) Toxicological test in a mouse model

Figure 3:
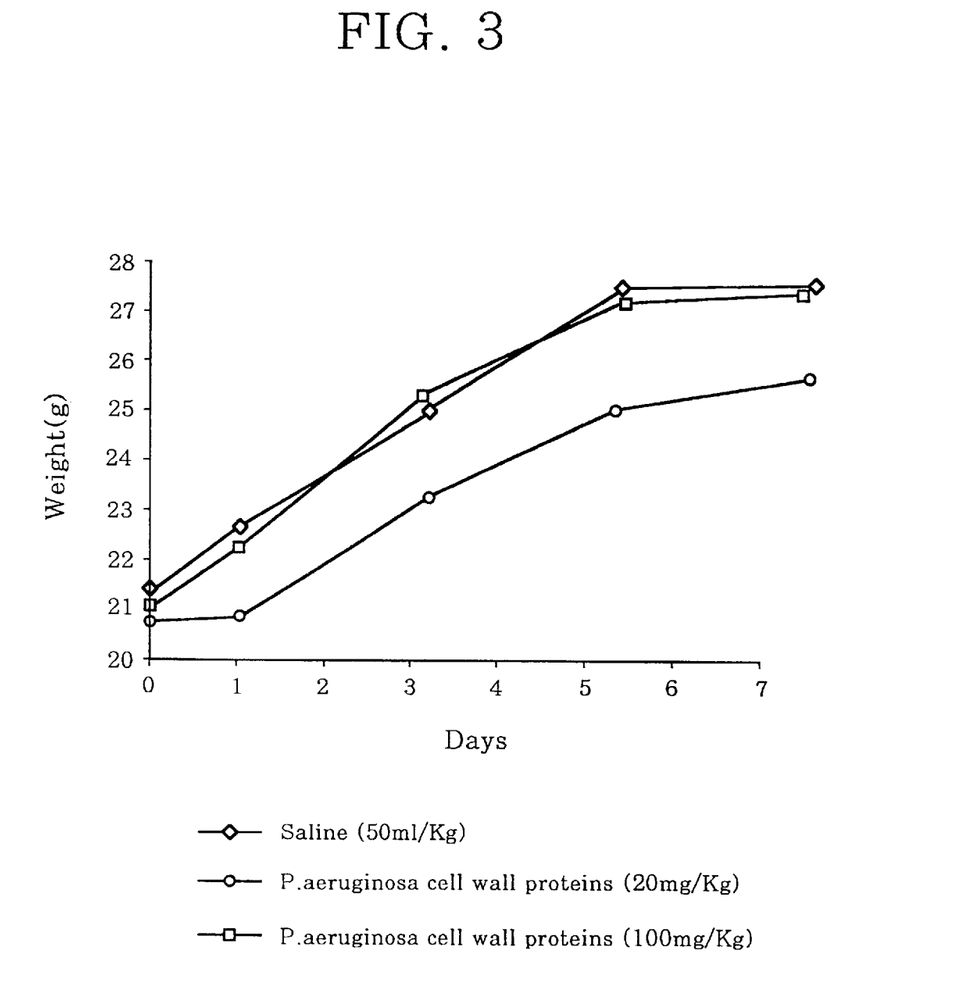
FIG. 3 is a graph representing the weight change in male mouse into which the cell wall protein of attenuated *Pseudomonas aeruginosa* strains are intravenously injected according to the present invention.

In this toxicological test, the experimental animals used were ICR male mice weighing from 20 to 22 g. To the test group, the protein source was intravenously injected in an amount of 20 mg/kg and 100 mg/kg. The control group was given physiological saline in an amount of 25 ml/kg. As can be seen from Table 12 and attached FIG. 3, the test group exhibited a slight inhibition to weight gain on the first day after administration but on and after the second day after administration showed normal growth and no special symptoms. In addition, even on and after the 7th day, specific changes or symptoms in each organ could not be found.

TABLE 12

Acute toxicological test for cell wall protein source of attenuated *Pseudomonas aeruginosa* strains

| Group | Dosage | Test Subjects | Survival/Test Subjects | Remarks |
|---|---|---|---|---|
| Test Group A | 20 mg/kg | 20 | 20/20 | No change of body weight |
| Test Group B | 100 mg/kg | 15 | 15/15 | Change of body weight only on the first day |
| Control Group | Physiological Saline | 15 | 15/15 | No change of body weight |

(2) Toxicological test in a rat model

In this test, the experimental animals used were Sparague-Dawley rats which were six week old weighing from 115 to 172 g (female) and from 143 to 230 g (male). To the test group each consisting of 5 male and 5 female rats, the protein source was orally or intramuscularly administered in an amount of 50 mg/kg, 25 mg/kg, 12.5 mg/kg, 6.25 mg/kg and 3.125 mg/kg, respectively. The control group was given physiological saline in an amount of 10 ml/kg. Changes in appearances, clinical signs and autopsy of the experimental rats were observed for 14 days after administration. The results indicated that there were also no differences in body weight, clinic signs and autopsy findings between all treated groups and control groups. Therefore, it was confirmed that the cell wall protein is a very safe compound.

(3) Toxicity to dogs by repeated intramuscular administration

Twenty-four pure-bred beagles were divided into four groups, each consisting of 3 male and 3 female animals. Three groups received protein source by intramuscular injection at 0.05, 0.15 and 0.45 mg/kg/day at a dosage volume of 0.4 ml/kg. The remaining four group acted as a control and received the vehicle alone for the same treatment period (i.e., 5 days per week for 4 weeks). Mortality, clinical signs, body weight and food consumption, and the like were observed with the aid of a testing facility supplied by Huntington Research Centre Ltd. (England).

Clinical signs considered to be related to treatment were restricted to swelling at the injection sites. There were observed for the animals from all dosage groups with a higher incidence being observed for those animals receiving 0.45 mg/kg/day. In addition, a larger number of animals from the treated groups were affected during weeks 2–4, than during the first week of treatment, indicating a possible sensitization response to the test substance. In the majority of instances, the swelling was apparent 1–2 hours after treatment, but was not generally apparent prior to administration of the next dose 24 hours later. There was no effect on bodyweight, food consumption, ophthalmoscopy, electrocardiography or hematology, biochemical and urinary parameters.

The histopathological examination revealed treatment-related changes at the injection sites at all dosages, particularly in the hindlimbs where both perivascular and intramuscular aggregations of inflammatory cells were seen. A higher incidence was seen in animals receiving 0.45 mg/kg/day. In addition, some associated atrophic changes were recorded for animals which had received 0.45 mg/kg/day.

In conclusion, the only treatment-related changes demonstrated by this study were relative to a local reaction to the test substance at the injection sites. Histopathology indicated this represented an inflammatory response, which in view of the nature of the protein vaccine, could be regarded as a pharmacological response. No evidence of any systemic toxicity was observed at any dosage level.

It is therefore concluded that dosage of cell wall protein up to and including 0.45 mg/kg/day were well tolerated over a period of 4 weeks in the beagle dog.

EXAMPLE 13
Determination of antigenicity of cell wall proteins

Cell wall proteins obtained by partial purification of attenuated *Pseudomonas aeruginosa* strains in the same manner as in Example 12 were used as an antigen and were intravenously injected into ICR mice three times at a seven-day interval in an amount of 0.1 mg/kg or 0.2 mg/kg to immunize the experimental animals. After one week from the final immunization, a small amount of blood was taken from each mouse of the group. The serum was separated from the collected blood and the formation of the antibodies was determined in accordance with the ELISA method [J. Clin. Microbiol. 15, pp. 1054–1058, 1982].

First, 100 $\mu$l of antigen prepared in Example 12, which was adjusted to a concentration of 0.1 mg/ml in a coating buffer (0.05M carbonate buffer solution consisting of NaHCO$_3$ 2.85 g, Na$_2$CO$_3$ 1.70 g, H$_2$O 1 l, pH 9.6), was added to each well of a 96-well microplate and then reacted either at room temperature for 2 hours or at 4° C. for 12 to 14 hours to bind the protein to each well.

After removing the aqueous solution, 200 $\mu$l of 1% bovine serum albumin (BSA) was added to the each plate well and then reacted at room temperature for one hour to block the remaining portion in the wells not bound to protein.

In this test, serum of a non-immunized mouse was used as an antibody for the control group. Upon completion of the reaction, the plate was washed again 5 to 6 times with a phosphate buffer solution (pH 7.0–7.2) and 100 μl of a secondary antibody, i.e. Rabbit-anti mouse Ig-Peroxidase Conjugate, was added to each well and allowed to react at room temperature for one hour.

Thereafter, the plate was vigorously washed 7 times or more with the same phosphate buffer washing solution (pH 7.0–7.2). As a substrate, 50 μl of ortho-phenylenediamine dihydrochloride, adjusted to a concentration of 0.3 to 0.4 mg/ml in citrate-phosphate buffer solution (0.1M Citrate-Phosphate buffer, pH 5.0), was added to each well of the plate and reacted for 20 minutes in the absence of light. Then 50 μl of 1 N-sulfuric acid was respectively added to stop the reaction in each well. Then, for each reaction solution the absorbance at 490 nm was measured by means of a spectrophotometer.

TABLE 13

Formation of antibodies against cell wall proteins of each microorganism (490 nm)

| Antigen content (mg/kg) | | antibody dilution | | | | |
|---|---|---|---|---|---|---|
| | 1/5 | 1/25 | 1/125 | 1/625 | 1/3125 | 1/15625 |
| Control Group | 0.16 | 0.15 | 0.29 | 0.47 | 0.41 | 0.43 |
| Test 0.1 | 0.29 | 0.25 | 0.32 | 0.52 | 1.1 | 1.2 |
| Group 0.2 | 0.76 | 0.67 | 0.50 | 0.49 | 1.3 | 1.4 |

As can be seen from Table 13, the test group administered 0.1 or 0.2 mg/kg antigen shows the binding activity 2 to 5 times higher than that in the control group.

EXAMPLE 14
Production of immunoglobulin for *Pseudomonas aeruginosa*

The protein solution obtained from Example 7 was administered to rabbit to produce the corresponding inunoglobulin. Although the cell wall protein obtained from attenuated *Pseudomonas aeruginosa* strain CFCPA 30720 was used as a typical example, the same method can be applied to the other attenuated *Pseudomonas aeruginosa* strains.

0.5 to 1 ml (containing 100 to 200 μg of cell wall protein) of the cell wall protein solution obtained from CFCPA 30720 strain in Example 7 was used to immunize albino rabbits three times at intervals of 7 days. Then blood was taken at regular intervals from each of the rabbits and the serum was separated. 100 ml of the separated rabbit serum was mixed with 300 ml of distilled water and the mixture was added to 500 g (wet weight) of DEAE-cellulose at 4° C. The resulting mixture was thoroughly shaken for one hour at 4° C., allowed to stand and then the supernatant was separated and removed. The remaining residue was washed three times with each 200 ml of 0.01M phosphate buffer solution ($Na_2HPO_4$ 1.15 g, $KH_2PO_4$ 0.2 g, KCl 0.2 g, NaCl 8.766 g, per liter, pH 8.0) to obtain 600 mg of immunoglobulin IgG having a purity of 96% or more.

EXAMPLE 15
Therapeutic effect of the immunoglobulin on *Pseudomonas aeruginosa* infection For immunoglobulins against *Pseudomonas aeruginosa* strains obtained in Example 14 above, their therapeutic effects on *Pseudomonas aeruginosa* infection were examined according to the following manner. 10 mice were used in each group.

$1.0–3.0 \times 10^7$ cells of each of the pathogenic *Pseudomonas aeruginosa* strains of Fisher immunotypes 1 to 7 were intraperitoneally injected into each mouse to cause *Pseudomonas aeruginosa* infection. Within 2 to 6 hours after the injection, the purified immunoglobulin for each strain was intraperitoneally injected into each mouse in an amount of 0.1 to 2 mg per mouse to examine the therapeutic effect thereof.

In the control group, 0.5 ml of physiological saline for injection was intravenously injected instead of immunoglobulin. In this test, the immunoglobulins used were CFCPA 10142, CFCPA 20215, CFCPA 30720 and CFCPA 60534, or a mixture of these 4 kinds of immunoglobulins in the ratio of equivalent amounts.

As a result, the control group which received only physiological saline exhibited a lethality rate of 50% or more within 48 hours and 100% after 72 hours. Whereas the test group which received the corresponding immunoglobulin exhibited a survival rate of 80% or more after 72 hours. Accordingly, it could be demonstrated that the immunoglobulin is effective for the treatment of infection caused by pathogenic *Pseudomonas aeruginosa* strain having the corresponding Fisher immunotype. However, no single immunoglobulin had much of an effect on an infection caused by pathogenic *Pseudomonas aeruginosa* strains having Fisher immunotypes 4 and 5.

On the other hand, the mouse group, which received the combination of 4 kinds of immunoglobulins in the ratio of 1:1:1:1 by weight, showed superior therapeutic effect even on Fisher types 4 and 5 of *Pseudomonas aeruginosa* strains due to their cross-reactivity. Accordingly, the combined immunoglobulin composition according to the present invention can be used as a therapeutic agent effective for infection caused by *Pseudomonas aeruginosa* strains having all Fisher immunotypes. The results of this experiment are summarized in Tables 14 and 15.

TABLE 14

Immunological protective effect according to the use of immunoglobulins individually or in a combination

| Strains used for preparing immunogoblin | Fisher immunotype | Immunological protective range |
|---|---|---|
| CFCPA 20215 strain alone | 2 | Fisher types 3, 7 |
| CFCPA 60534 strain alone | 6 | Fisher types 3, 7 |
| CFCPA 10142 strain alone | 1 | Fisher types 2, 1 |
| CFCPA 30720 strain alone | 3 | Fisher type 6 |
| Mixed strain of CFCPA 20215, CFCPA 60534, CFCPA 10142, and CFCPA 30720 | 2, 6, 1, 3 | Fisher types 3, 7, 2, 1, 6, 4 and 5 |

TABLE 15

Mutual relation of immunological protection of immunoglobulin against *Pseudomonas aeruginosa* strains

TABLE 15-continued

Mutual relation of immunological protection of immunoglobulin against *Pseudomonas aeruginosa* strains

| | |
|---|---|
| CFCPA 10142 strain-induced immunoglobulin | Immunological protection against Fisher type 1 and Fisher type 2 |
| CFCPA 30720 strain-induced immunoglobulin | Immunological protection against Fisher type 6 |
| Combination of the above 4 kinds of immunoglobulins | Immunological protection against all Fisher types 1 to 7 |

EXAMPLE 16
Therapeutic effect of the combined immunoglobulins on *Pseudomonas aeruginosa* infection 4 kinds of attenuated *Pseudomonas aeruginosa* strains selected in Example 15, i.e., CFCPA 10142, CFCPA 20215, CECPA 30720 and CFCPA 60534 were cultivated and extracted according to the same procedures as Examples 5, 6 and 7 to obtain the combined composition of cell wall proteins. The cell wall proteins were then immunized three times at intervals of one week in an amount of 1.5 to 2 mg into goat according to the same manner as Example 15 to obtain the combined *Pseudomonas aeruginosa* immunoglobulins in a large quantity which was purified according to the known method [see, Practical Immunology, 3rd ed., (1989), pp 292–294].

In order to determine the immunological protective effect and therapeutic effect of the purified and combined immunoglobulin obtained above on pathogenic *Pseudomonas aeruginosa* of various Fisher immunotypes, pathogenic *Pseudomonas aeruginosa* strains having each immunotype were inoculated into a mouse group (six groups: 20 mice per group) into which the combined immunoglobulin composition was previously injected three times, and another mouse group (six groups: 10 mice per group which received no immunoglobulin composition) in an amount of 1.0 to 3.0× $10^7$ cells per mouse to observe the immunological protective effect of the combined immunoglobulin. In addition, in another mouse group (six groups: 10 mice per group) pathogenic *Pseudomonas aeruginosa* was first inoculated and after 2 to 6 hours the combined immunoglobulin composition obtained above was intravenously injected in an amount of 0.1 to 5 mg per mouse weighing about 20 to 25 g to observe the therapeutic effect of the immunoglobulin composition according to the present invention.

As a result thereof, it could be demonstrated that the combined immunoglobulin composition according to the present invention exhibits an immunological protective effect of 80%, or more, and a therapeutic effect of 75% or more (determined as the survival rate (%) after 7 days) while all the control groups have died within 3 days.

Accordingly, it can be determined that the combined immunoglobulin composition of the preset invention can be used as a useful medicinal agent showing both excellent therapeutic effect and immunological protective effect.

EXAMPLE 17
Formulation of imununoglobulin

The combination of cell wall proteins which were obtained by cultivation and extraction of 4 kinds of attenuated *Pseudomonas aeruginosa* strains selected in Example 15, i.e., CFCPA 10142, CFCPA 20215, CFCPA 30720 and CFCPA 60534 according to the same manner as Examples 5 to 7, was administered to male goat in the same manner as Example 16 to obtain the combined *Pseudomonas aeruginosa* immunoglobulin which was separated and purified, and then formulated using various pharmaceutically acceptable carriers so that 1 to 100 mg of antibody immunoglobulin can be administered per kg of body weight. The formulated immunoglobulin was administered to mice infected with *Pseudomonas aeruginosa* to determine the efficacy of the inununoglobulin depending on the kinds of carriers used the immunoglobulin. As a result of this, in the case of liquid formulation, the immunoglobulin preparation with physiological saline for injection or phosphate buffer solution as a carrier exhibits a high efficacy and in the case of lyophilized formulation the use of mannitol, saccharose or lactose as a carrier provides the high efficacy of the immunoglobulin preparation. On the other hand, in a lyophilized formulation, the use of human albumin together with *Pseudomonas aeruginosa* immunoglobulin according to the present invention lowers the efficacy of immunoglobulin and in the case of liquid formulation the use of aluminum hydroxide as a pharmaceutical carrier shows low efficacy. The test results are summarized in Table 16.

TABLE 16

Efficacy of *Pseudomonas aeruginosa* Immunoglobulin depending on pharmaceutical carriers

| Formulation type | Constituents | Efficacy |
|---|---|---|
| Lyophilized formulation | Purified combined immunoglobulin composition + mannitol (5–20%) | ++++ |
| | Purified combined immunoglobulin composition + lactose (5–20%) | +++ |
| | Purified combined immunoglobulin composition + saccharose (5–20%) | +++ |
| | Purified combined immunoglobulin composition + human albumin (1–5%) | ++ |
| Liquid formulation | Purified combined immunoglobulin composition + physiological saline | ++++ |
| | Purified combined immunoglobulin composition + distilled water for injection | ++++ |
| | Purified combined immunoglobulin composition + phosphate buffer solution | ++++ |
| | Purified combined immunoglobulin composition + aluminum hydroxide + solvent | ++ |

EXAMPLE 18
Efficacy of the formulated immunoglobulin composition

The formulated immunoglobulin with a phosphate buffer solution, as identified to provide the high efficacy from the test result of Example 17, was examined to determine the efficacy as a prophylactic and therapeutic agent for a secondary cutaneous infection in laceration, burn, trauma, and the like. A mouse received a burn according to the burn test procedure [See, J. Infect. Dis. 131, pp. 688–691, 1975]. The liquid preparation containing 0.5 to 1 mg of combined *Pseudomonas aeruginosa* immunoglobulin per 1 ml of phosphate buffer solution was formulated into a spray, which was then applied to the burn portion of the mouse in the test group to determine the effect thereof in comparison with that in the control group having no treatment with the immunoglobulin spray. As a result of this experiment, the mouse group treated with the immunoglobulin-phosphate buffer solution spray shows remarkably higher survival rate than the non-treated group. Accordingly, it can be demonstrated that the *Pseudomonas aeruginosa* immunoglobulin-containing preparation according to the present invention exhibits a superior protective effect and a superior therapeutic effect on *Pseudomonas aeruginosa* infection. The results of this experiment is described in the following Table 17.

TABLE 17

Result of burn testing

| Treatment | Number of Mouse | P. aeruginosa inoculation | Survival rate | | | |
|---|---|---|---|---|---|---|
| | | | 24 hrs | 48 hrs | 72 hrs | 96 hrs or more |
| Burn (treated with immunoglobulin) | 20 | local inoculation | 20/20 | 19/20 | 16/20 | 16/20 |
| Burn (not treated with immunoglobulin) | 20 | local inoculation | 18/20 | 4120 | 0/20 | — |
| Control group | 10 | no inoculation | 10/10 | 10/10 | 10/10 | 10/10 |

As described above, each attenuated *Pseudomonas aeruginosa* strain according to the present invention is considerably safe relative to the wild or pathogenic species. In addition, since the cell wall proteins thereof exhibit an excellent safety and cross-protective property and also a superior neutralizing antibody formation capacity, the cell wall proteins can be used not only as a vaccine for prophylaxis against *Pseudomonas aeruginosa* infection but also as an antibody inducer in the experimental animal to produce immunoglobulin which can used as a therapeutic agent for *Pseudomonas aeruginosa* infection. It can be seen that attenuated *Pseudomonas aeruginosa* strains according to the present invention are very useful microorganisms for preparing a prophylactic vaccine and a therapeutic agent for *Pseudomonas aeruginosa* infection.

What is claimed is:

1. In a process for preparing a vaccine as a prophylactic agent against *Pseudomonas aeruginosa* infection comprising the steps of:
   a) preparing pure isolated cells of attenuated *Pseudomonas aeruginosa* strains;
   b) treating the cells of *Pseudomonas aeruginosa* with an organic solvent to inactivate the cells and remove lipid components;
   c) subjecting the cells thus treated to extraction to give an extract;
   d) subjecting the resulting extract to fractionization and purification by ultrafiltration and ultracentrifugation to select a specific fraction of proteins;
   e) recovering the selected fraction of proteins; and
   f) preparing a vaccine using the selected fraction of proteins, the improvement comprising performing step (c) by introducing the solvent-treated cells in step (b) into a buffer solution, allowing the resulting mixture to stand and be stirred at 4° C. at 50 to 150 rpm so that cell wall of microorganism of *Pseudomonas aeruginosa* is not destroyed, thereby providing an extract which does not contain any cytoplasmic substances including alkaline protease, elastase, and exotoxin A or DNA, and selecting in step (d) the specific fraction of protein having a molecular weight of 10,000 to 100,000 and containing substantially no lipopolysaccharide.

2. The process according to claim 1, wherein step (c) is performed by introducing the solvent-treated cells in step (b) into a buffer solution, allowing the resulting mixture to stand and by stirring the same gently.

3. The process according to claim 2, wherein the stirring is performed at 4° C. with a mixer or homogenizer which operates at 50 to 150 rpm.

4. The process according to claim 1, wherein the buffer solution is selected from the group consisting of a phosphate buffer solution and a tris buffer solution.

5. The process according to claim 1, wherein inspection is conducted on the extract, during or after step (c), as to whether the cells have been destroyed by ascertaining the presence of lactate dehydrogenase or hexokinase as a cytoplasmic marker enzyme.

6. The process according to claim 1, wherein the strains used in step a) are selected from the group consisting of *Pseudomonas aeruginosa* CFCPA 10142, CFCPA 20215, CFCPA 30720, CFCPA 40057, CFCPA 50243, CFCPA 60534, and CFCPA 70018.

7. The process according to claim 1, wherein the organic solvent used in step b) is selected from the group consisting of acetone, chloroform, ethanol, and butanol.

* * * * *